United States Patent [19]
Aota et al.

[11] Patent Number: 5,779,982
[45] Date of Patent: Jul. 14, 1998

[54] AUTOMATIC SAMPLE PREPARING APPARATUS

[75] Inventors: Kensaku Aota, Hyogo; Jun Toyoda, Kobe; Yoshihiko Miki, Kakogawa; Masakazu Kondo, Kobe, all of Japan

[73] Assignee: TOA Medical Electronics Co., Ltd., Hyogo, Japan

[21] Appl. No.: 625,007

[22] Filed: Mar. 29, 1996

[30] Foreign Application Priority Data

Mar. 31, 1995 [JP] Japan .................................. 7-075523

[51] Int. Cl.⁶ .................................................. B01L 3/00
[52] U.S. Cl. .................. 422/100; 422/65; 422/67; 422/102; 422/104; 118/100; 118/120
[58] Field of Search ..................... 422/100, 102, 422/65, 67, 99, 104; 118/100, 120, 415, 500

[56] References Cited

U.S. PATENT DOCUMENTS

| | | | |
|---|---|---|---|
| 3,880,111 | 4/1975 | Levine et al. | 118/4 |
| 4,349,275 | 9/1982 | Ayotte et al. | 356/36 |
| 4,494,479 | 1/1985 | Drury et al. | 118/120 |
| 5,209,903 | 5/1993 | Kanamori et al. | 422/65 |
| 5,234,559 | 8/1993 | Collier et al. | 204/182.8 |
| 5,270,012 | 12/1993 | Kanamori et al. | 422/102 |
| 5,356,595 | 10/1994 | Kanamori et al. | 422/65 |
| 5,567,594 | 10/1996 | Calenoff | 435/7.32 |

FOREIGN PATENT DOCUMENTS

| | | |
|---|---|---|
| 56-52244 | 5/1981 | Japan . |
| 3-094159 | 4/1991 | Japan . |
| 370355 | 7/1991 | Japan . |

*Primary Examiner*—Harold Y. Pyon
*Attorney, Agent, or Firm*—Birch, Stewart, Kolasch & Birch, LLP

[57] ABSTRACT

An automatic sample preparing apparatus which can automatically perform all the steps of a sample preparation process from smearing of sample onto a slide glass to dyeing the smeared sample and with which there is no wasting of dyeing liquid even when only a small number of samples are to be dyed and the degree of freedom of slide glass handling and control is high. The apparatus can include a smearing part, cassettes, a carrying part, a loading part, a dyeing part and a storing part. The smearing part functions to smear samples onto slide glasses. Each cassette has a holding part which can hold slide glasses and a liquid and a pair of hanging support parts connected to this holding part. The carrying part carries the cassettes. The loading part loads the slide glasses one by one into the cassettes. The dyeing part performs dyeing of the smeared sample on the slide glasses. The storing part stores cassettes containing slide glasses with sample smeared thereon and dyed.

11 Claims, 16 Drawing Sheets

AUTOMATIC SAMPLE PREPARING APPARATUS

BACKGROUND OF THE INVENTION

1. Field of the Invention

This invention relates to an automatic sample preparing apparatus, and particularly to an automatic sample preparing apparatus for preparing samples by automatically smearing samples on slide glasses and/or automatically dyeing samples smeared on slide glasses.

2. Description of the Prior Art

Conventionally, as an automatic sample preparing apparatus for preparing samples by automatically smearing blood on slide glasses for sample use, there has been known an apparatus (apparatus A) disclosed in Japanese Unexamined Patent Publication No. H.3-94159 having a supply part containing multiple slide glasses in a stack, a moving member for moving these slide glasses one at a time in a transverse direction from the supply part, a carrying part for carrying slide glasses moved by this moving part to subsequent steps and a holding part for holding a plurality of slide glasses of which processing has been completed, wherein dropping of blood from a fine tube, smearing of the blood with a drawing glass and drying with a fan are carried out in the carrying part.

Also, as an automatic sample preparing apparatus for preparing samples by automatically carrying out dyeing on slide glasses on which blood has been smeared, there has been known an apparatus (apparatus B) disclosed in Japanese Unexamined Utility Model Publication No. H.3-70355 comprising a mechanism for feeding slide glasses into a dyeing tank and a controlling part for controlling this mechanism for dyeing blood smeared on the slide glasses by immersing them in the dyeing tank, wherein the controlling part memorizes the number of times the dyeing liquid in the dyeing tank has been used and the number of samples dyed and changes the dyeing time according to these numbers, and an apparatus (apparatus C) disclosed in Japanese Unexamined Utility Model Publication No. S.56-52244 having a plurality of vessels (dyeing tanks) into each of which one smeared sample is inserted and thereby dyed wherein a belt having the vessels fixed thereto is moved intermittently one step at a time.

However, with the apparatus A, although smeared samples can be prepared efficiently and well, when the smeared samples are to be dyed this must be done by a separate dyeing apparatus.

Apparatus B carries out dyeing by holding 10 to 50 slide glasses on which blood has been smeared in a holding vessel for dyeing and immersing this in a dyeing tank containing dyeing liquid, and by making the dyeing time longer in correspondence with the number of times the dyeing liquid has been used it is possible to keep the degree of dyeing constant; however, there has been the problem that a large quantity of dyeing liquid is required even when just a few slide glasses are to be dyed. That is, because the slide glass holding vessel (holding vessel for dyeing) used in the apparatus B is of a size enabling it to hold up to 50 slide glasses, there has been the problem that even when just a few slide glasses are to be dyed it is necessary to use the same large quantity of dyeing liquid as when 50 slide glasses are to be dyed. The apparatus C, on the other hand, has the merit that even when the number of samples to be dyed is small there is no wasting of dyeing liquid, but with this apparatus there has been the problem that because the dyeing tanks, which are vessels for dyeing, are fixed to a belt, the degree of freedom of handling and control of slide glass takeout, input and moving operations has been low.

Also, because the apparatus B and the apparatus C only dye slide glasses on which blood has already been smeared, the step of smearing the blood onto the slide glasses must be done by a separate apparatus.

SUMMARY OF THE INVENTION

The present invention was devised in view of these kinds of problem, and an object of the invention is to provide an automatic sample preparing apparatus which can perform all the steps from smearing to dyeing automatically and with which there is no wasting of dyeing liquid and the degree of freedom of slide glass handling and control is high.

To achieve the above-mentioned object and other objects, the invention provides an automatic sample preparing apparatus comprising a smearing part for smearing a sample (such as blood, urine and liquid specimen including cells, etc.) on a slide glass, a carrying part for having removably set thereon and carrying at least one slide glass holding cassette having a holding part capable of holding a slide glass and a liquid, a loading part for loading slide glasses into the cassettes one by one and a dyeing part for supplying dyeing liquid to the cassettes and thereby dyeing the sample smeared on the slide glasses.

In the invention, a novel slide glass holding cassette comprising hanging support parts connected to the holding part for supporting this holding part in a downwardly hanging state is preferably used.

Also, the automatic sample preparing apparatus preferably further comprises a storing part for storing cassettes holding smeared slide glasses fed out from the dyeing part.

As the slide glasses for sample use, ones of various sizes and made of various materials, ones having frosted portions and ones not having frosted portions and ones with their frosted portions colored and ones with their frosted portions not colored are suitably selected and used. One example is a slide glass of length 76 m, width 26 mm and thickness 0.9 to 1.2 mm having cut corners and ground edges and a colored frosted portion 15 to 20 mm long.

A slide glass holding cassette preferably used in this invention has a holding part and a hanging support part. The holding part is capable of holding a predetermined number of slide glasses and a liquid such as a dyeing liquid or a washing liquid. The hanging support part is connected to the holding part and support the holding part in a hanging state for purposes such as carrying and storing. This cassette is for example made of plastic and transparent and flat in overall shape.

DETAILED DESCRIPTION OF THE PREFERRED EMBODIMENT

Figure 1:
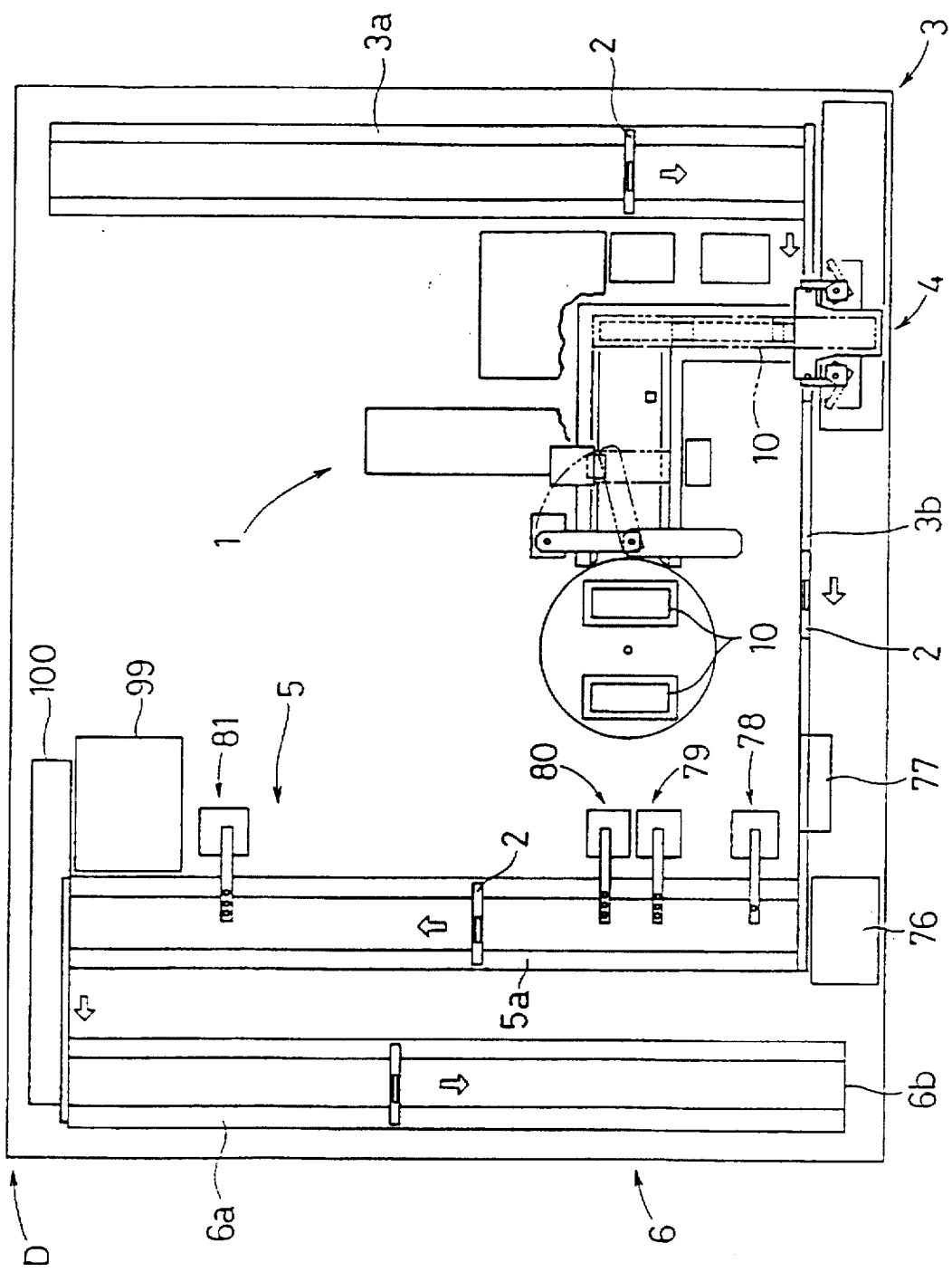
FIG. 1 is a plan view showing the overall construction of an automatic sample preparing apparatus according to a preferred embodiment of the invention.

The holding part of the cassette preferably comprises a main space capable of holding a slide glass and a liquid, an auxiliary space for liquid supply and discharge adjacent to this main space and connected to the main space and a bottom wall extending across the main space and the auxiliary space and sloping downward from the main space to the auxiliary space. In this case, the main space and the auxiliary space are divided by for example a partition wall, the main space has a space for receiving for example one slide glass and the auxiliary space has a space into which can be inserted a pipette or a tube or the like for supplying or discharging for example a dyeing liquid or a washing liquid. Also, the sloping bottom wall promotes the effective supply and discharge of dyeing liquid and the like to and from the auxiliary space and prevents surface tension in gaps between the lower part of the slide glass held in the main space and the side walls of the main space from causing dyeing liquid to remain in those gaps.

The holding part of the cassette also preferably comprises a positioning part for holding the slide glass in a position on one side of the inside of the holding part instead of the above-mentioned partition wall. In this case, the positioning part for example consist of slide glass holding guides provided in a slide glass receiving opening of the holding part.

The cassette is preferably provided with a mis-setting preventing part for preventing the cassette from being set other than in a predetermined state. Here, a predetermined state means a state wherein the cassette is set in a prescribed position with a prescribed orientation in for example the carrying part for carrying the cassettes. This mis-setting preventing part may be provided in the above-mentioned holding part or may be provided on the above-mentioned hanging support part or may be provided extending across the holding part and the hanging support part. One method of providing a mis-setting preventing part is to make the shape of the front of the cassette asymmetrical.

The smearing part in this invention performs smearing of blood on a slide glass. The method of this smearing may be a wedge method (using another glass) or a spinner method (a centrifugal method). Preferably the smearing part has a rotatable slide glass supply table, a plurality of slide glass supply parts are provided on the table, the table is rotationally driven and slide glasses are supplied one after another from the plurality of slide glass supply parts and smeared one at a time. If this kind of construction is adopted, if different types of slide glass are loaded into the plurality of slide glass supply parts, desired slide glasses for smearing can be selected from the plurality of types.

The carrying part has removably set thereon and carries normally more than one but in the case of so-called interrupt carrying just one cassette (having a holding part capable of holding a slide glass for sample use and a liquid) not holding a slide glass or holding a slide glass. The carrying is carried out for example by an intermittently moving belt conveyor having a set of two belts disposed in parallel with each other with a predetermined spacing therebetween. At this time, if the cassette has the hanging support part, the cassette is carried hanging from the two belts by the hanging support part.

The loading part loads slide glasses one by one into cassettes on the carrying part. The loading part preferably comprises a slide glass holding part for holding a smeared slide glass substantially horizontally, a stopping mechanism for temporarily stopping one cassette on the carrying part at a time, a pivoting mechanism for reversibly pivoting to a substantially horizontal position a cassette temporarily stopped by the stopping mechanism and a moving and inserting mechanism for moving a smeared slide glass held by the slide glass holding part and inserting it into the cassette pivoted to a substantially horizontal position by the pivoting mechanism.

The dyeing part supplies dyeing liquid to the cassettes and thereby carries out dyeing of the smeared blood on the slide glasses. As dyeing processes there are for example the steps of May Grünwald fixing, May Grünwald dyeing, Gimza dyeing and washing. The dyeing part preferably has pipettes capable of being inserted into the cassettes. When the cassettes each have a space into which these pipettes can be inserted (for example a main space for holding a slide glass and a liquid and an auxiliary space for liquid supply and discharge adjacent to this main space and connected to the main space), the pipettes are inserted into this space in the cassette and used to supply and discharge dyeing liquid and washing liquid or the like.

An automatic sample preparing apparatus according to the invention preferably has a storing part for storing cassettes holding smeared slide glasses fed out from the dyeing part. When a predetermined number of cassettes collect in this storing part, they are taken out of the storing part.

An automatic sample preparing apparatus according to the invention normally carries out all steps from smearing to dyeing automatically, but because the cassettes can be manually put onto and removed from the carrying part, the smearing part and the storing part, the apparatus can alternatively carry out smearing only or dyeing only.

A preferred embodiment of the invention will now be described with reference to the accompanying drawings. The invention is not limited by this preferred embodiment.

In FIG. 1, an automatic sample preparing apparatus D comprises a smearing part 1 for smearing blood onto sample slide glasses 10; cassettes 2 for holding slide glasses; a cassette feed belt 3a which is a double belt and moves forward and a cassette crossfeed belt 3b which is a single belt and moves from right to left, these two belts constituting a carrying part 3 (3a, 3b) for having removably attached thereto and carrying one or a plurality of the cassettes 2; a loading part 4 for loading smeared slide glasses 10 one by one into cassettes 2 on the cassette crossfeed belt 3b of the carrying part 3; a dyeing part 5 for feeding dyeing liquid into cassettes 2 carried to the dyeing part 5 by the cassette crossfeed belt 3b and thereby dyeing blood smeared on the slide glasses 10; and a storing part 6 for storing cassettes 2 fed out from the dyeing part 5 and containing smeared slide glasses 10.

Figure 2:
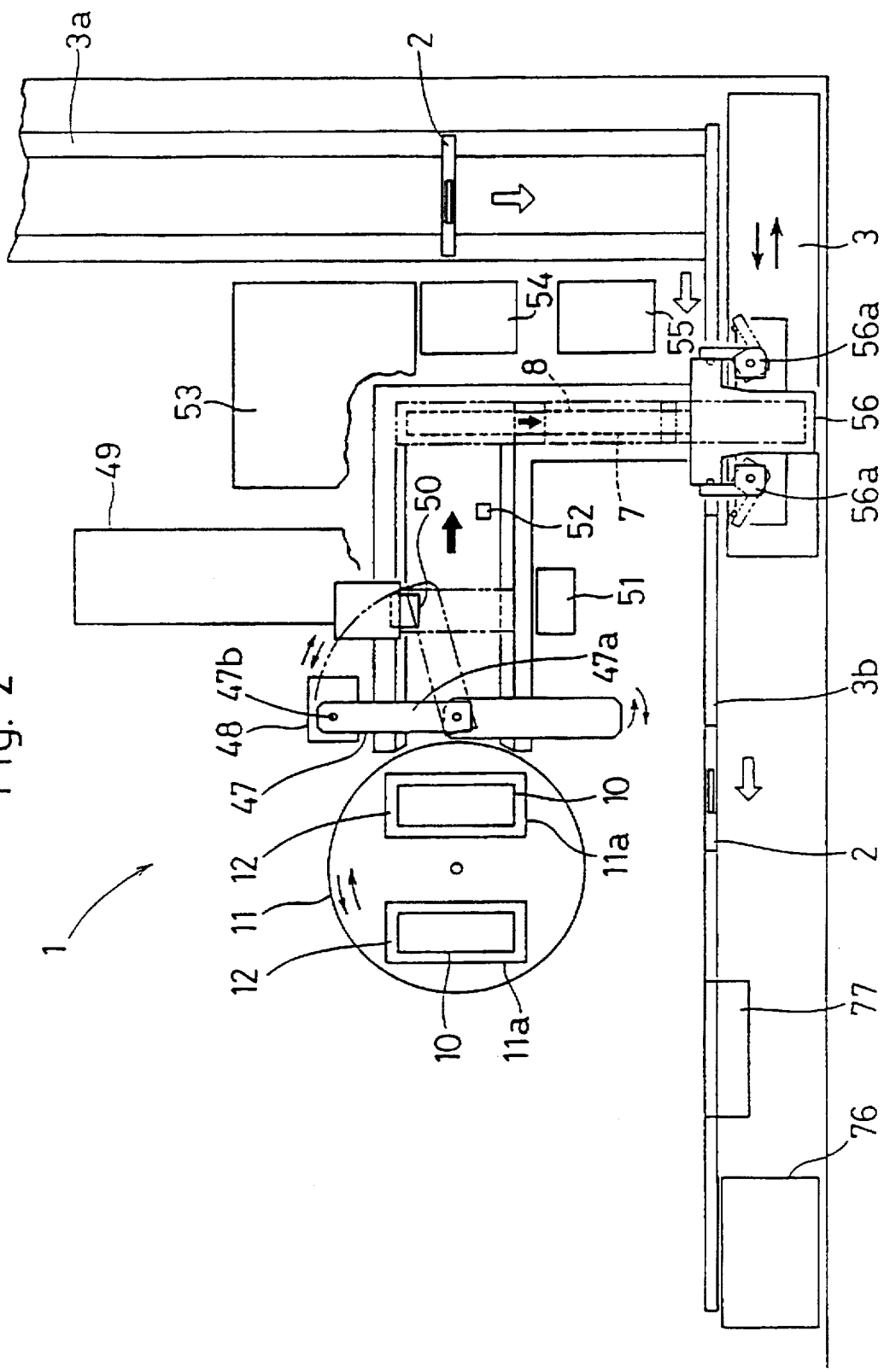
FIG. 2 is a plan view showing the construction of a part of the automatic sample preparing apparatus of FIG. 1.

As shown in FIG. 2, the smearing part 1 has a slide glass supply turntable 11 intermittently rotatable in forward and reverse directions; two slide glass supply holes 11a (in 'position 1' and 'position 2') are provided in the turntable 11, and two rectangular parallelepiped shaped slide glass supply cassettes 12, each capable of holding a stack of 100 slide glasses 10, are fitted in these slide glass supply holes 11a. A takeout hole is provided at the bottom of each of these cassettes 12, and the lowest slide glass 10 is taken out through this takeout hole.

The slide glasses held in the cassettes 12 are 76 mm long, 26 mm wide and 1.0 mm thick; they have had their corners cut and their edges ground and have frosted portions, the length of the frosted portions being 15 mm. Slide glasses 10 with their frosted portions colored white are held in the left side cassette 12 in FIG. 2 and slide glasses 10 with their frosted portions colored red are held in the right side cassette 12. The frosted portions are colored white and red here so as to provide two types of slide glass 10 which can be used to distinguish male/female, inpatient/outpatient, morning/afternoon or sampler/manual samples or the like.

Figure 3:
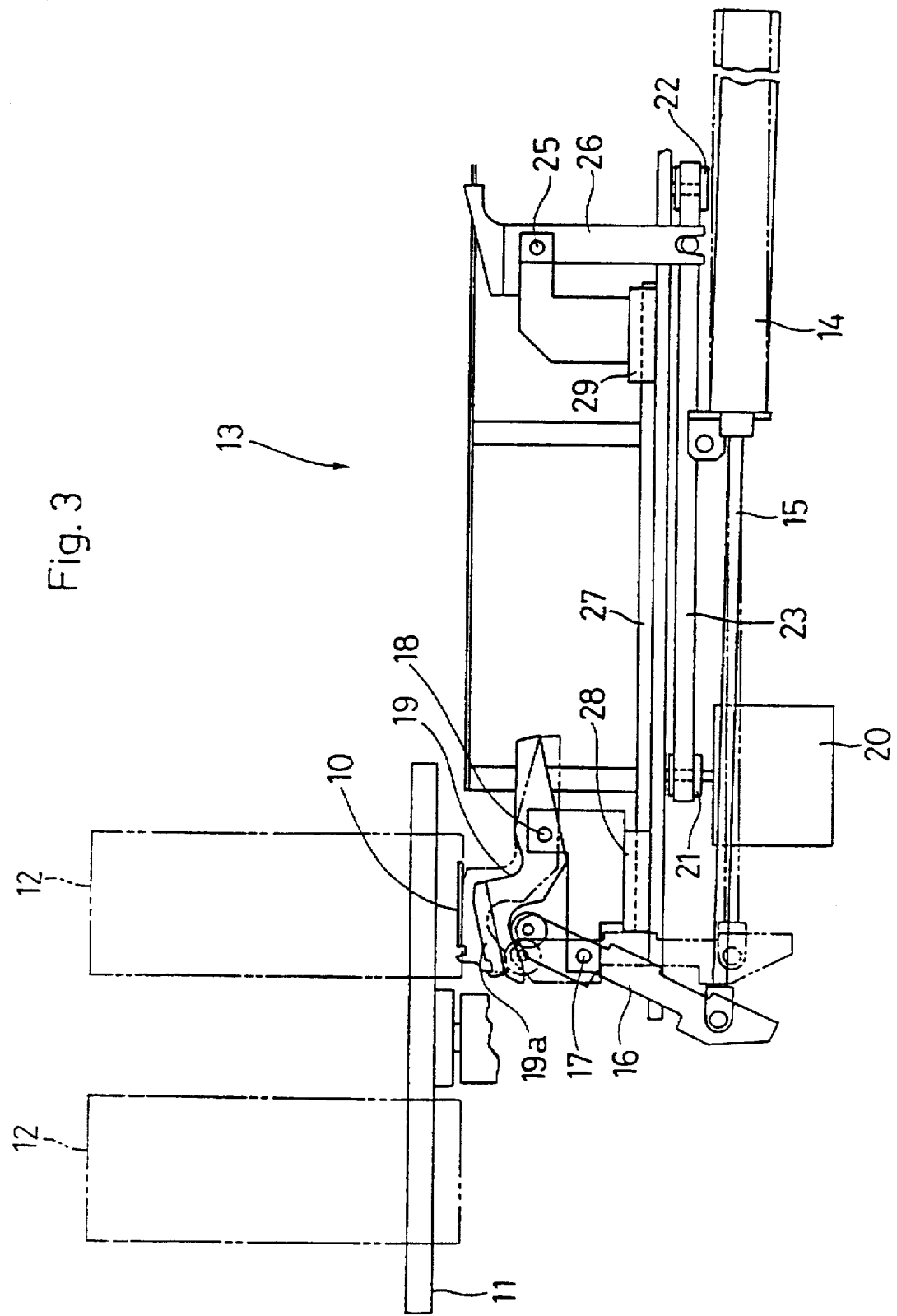
FIG. 3 is a side view showing a state before a slide glass is taken out of a slide glass supply cassette by a slide glass takeout mechanism in the automatic sample preparing apparatus of FIG. 1.
Figure 4:
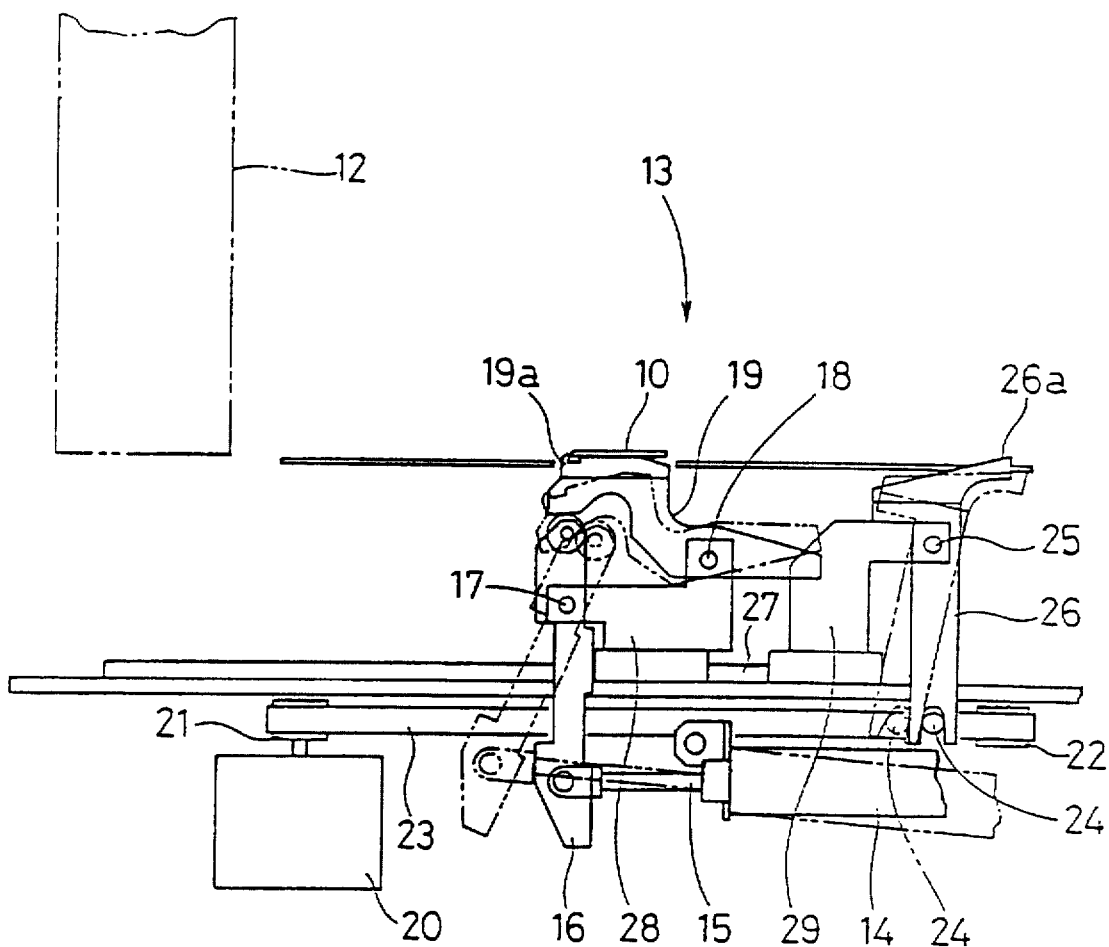
FIG. 4 is a side view showing a state after a slide glass is taken out of the slide glass supply cassette by the slide glass takeout mechanism of FIG. 3.
Figure 5:
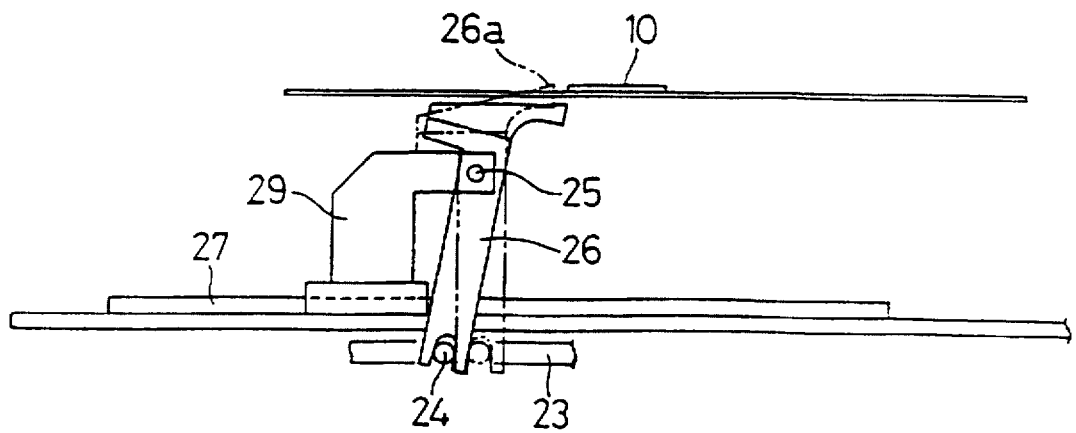
FIG. 5 is a side view showing a state of a slide glass being carried by the slide glass takeout mechanism of FIG. 3 to a position for printing.

When a slide glass 10 is taken out of one of the cassettes 12, this slide glass 10 is carried to a predetermined position for smearing and then after blood is smeared on it the slide glass 10 is carried to a predetermined position for printing as shown in FIG. 3 through FIG. 5.

In FIG. 3, a slide glass takeout mechanism 13 is disposed below the turntable 11. The slide glass takeout mechanism 13 comprises a piston rod 15 made to reciprocate to the left and right by an air cylinder 14, a first arm 16 pivotally supported by the left end of the piston rod 15 and a support shaft 17 thereabove, a first lever 19 abutting with the upper end of the first arm 16 and pivotally supported by a support shaft 18, a motor 20 disposed behind the piston rod 15, a belt 23 strung horizontally around left and right pulleys 21 and 22 and driven to the left and right by the motor 20 and a second arm 26 pivotally supported by a support shaft 24 attached to the belt 23 and a support shaft 25 thereabove.

The two support shafts 17 and 18 are parts of a first slider 28 which is horizontally disposed above the belt 23 and moves to the left and right guided by a guide rail 27. The support shaft 25 is part of a second slider 29 which also moves to the left and right guided by the guide rail 27.

Referring to FIG. 3, when the piston rod 15 is retracted by the air cylinder 14 from the position in which it is shown with solid lines to the position in which it is shown with two-dot chain lines, the first arm 16 pivots counterclockwise about the support shaft 17 and becomes vertical as shown with two-dot chain lines. When this happens, the upper end of the first arm 16 causes the first lever 19 to pivot clockwise about the support shaft 18 and the head 19a of the first lever 19 is lifted up, as shown with two-dot chain lines. As a result, the head 19a of the first lever 19 abuts with the lower surface of the slide glass 10 positioned at the bottom of the right-side cassette 12 fitted to the turntable 11.

When the piston rod 15 retracts further, the first lever 19 is moved to the right by the first arm 16 and the first slider 28 and the head 19a of the first lever 19 takes this slide glass 10 out of the cassette 12 through the takeout hole thereof and brings it to a first predetermined position (a position for smearing) shown with solid lines in FIG. 4. Next, when the piston rod 15 extends, the first arm 16 pivots clockwise about the support shaft 17 and reaches the position in which it is shown with two-dot chain lines in FIG. 4. When this happens, the first lever 19 pivots counterclockwise about the support shaft 18 and the head 19a of the first lever 19 descends as shown with two-dot chain lines. When the piston rod 15 then extends further, the first lever 19 with its head 19a thus lowered moves to the left together with the first arm 16 and the first slider 28.

When the front side of the belt 23 moves to the left and the support shaft 24 moves from the position in which it is shown with a solid line to the position in which it is shown with a two-dot chain line, the second arm 26 pivots clockwise about the support shaft 25 and the head 26a of the second arm 26 becomes horizontal as shown with two-dot chain lines. When the front side of the belt 23 then moves further to the left, the second arm 26 with its head 26a lowered moves to the left together with the second slider 29.

When the second arm 26 has passed the above-mentioned first predetermined position the movement of the belt 23 temporarily stops. At this time, the second arm 26 is in the position in which it is shown with solid lines in FIG. 5. Next, the front side of the belt 23 moves to the right and the support shaft 24 moves to the position in which it is shown with a two-dot chain line in FIG. 5. When this happens, the second arm 26 pivots counterclockwise about the support shaft 25 and as shown with two-dot chain lines the right end of the head 26a of the second arm 26 rises to the height of the slide glass 10 which is in the first predetermined position. Then, as a result of the front side of the belt 23 moving further to the right, the second arm 26 with the right end of its head 26a thus raised moves to the right together with the second slider 29. When this happens, the slide glass 10 in the first predetermined position is pushed to the right by the right end of the head 26a of the second arm 26 and is carried to a second predetermined position (a position for printing), which is a final position.

Next, the structure of a slide glass holding cassette 2 will be described with reference to FIG. 6 through FIG. 11.

The cassette 2 is a black and semi-transparent, tall and flat container made of polysulfon, and has one holding part 31 capable of holding one slide glass 10 and a liquid and left and right hanging support parts 32 and 33 which are connected to the upper part of this holding part 31 and are for supporting the holding part 31 in a hanging state. The holding part 31 has a vertical left side wall 31a, a vertical right side wall 31b, a sloping bottom wall 31c, a vertical front wall 31d and a vertical rear wall 31e, and has a space enclosed by these walls 31a to 31e.

This space is made up of a main space 34 capable of holding a slide glass 10 and a liquid and an auxiliary space 35 adjacent to the main space 34 and connected to the main space 34 for supply and discharge of a liquid (a dye liquid or a washing liquid or the like). The bottom wall 31c extends across the main space 34 and the auxiliary space 35 and slopes at about 10 degrees downward from the main space 34 to the auxiliary space 35.

The main space 34 and the auxiliary space 35 are divided by an upper left slide glass holding guide 36 provided on the left side of a slide glass receiving hole 40 in the holding part 31 and a lower left slide glass holding guide 37 provided below this upper left guide 36. An upper right slide glass holding guide 38 is provided on the right side of the slide glass receiving hole 40 and connected to the right side hanging support part 33, and a lower right slide glass holding guide 39 is provided below the upper right guide 38 at the same height as the lower left guide 37. The upper left guide 36, the lower left guide 37, the upper right guide 38 and the lower right guide 39 function as positioning parts for holding the slide glass 10 in the main space 34 on the right side of the inside of the holding part 31.

A pin 42 made of polysulfon and extending between the front wall 31d and the rear wall 31e is disposed between the lower left guide 37 of the main space 34 and the bottom wall 31c. This pin 42 has the function of holding the lower end of the slide glass 10 received into the main space 34 away from the bottom wall 31c.

The height of the left and right hanging support parts 32 and 33 is about 20% of the height of the holding part 31. A pipette insertion opening 41 for inserting pipettes for injecting and sucking up dye liquid and washing liquid and the like is formed between the left side hanging support part 32 and the upper left guide 36. The pipette insertion opening 41 becomes narrower downward and is connected to the auxiliary space 35. That is, a downwardly sloping portion 32a whose angle of inclination from the horizontal is about 60° is provided on the left side hanging support part 32 facing the upper left guide 36 and a downwardly sloping portion 31f whose angle of inclination from the horizontal is about 75° is provided at the top of the left side wall 31a of the holding part 31 and is connected to the downwardly sloping portion 32a of the hanging support part 32.

The downwardly sloping portion 31f at the top of the left side wall 31a of the holding part 31 functions as a missetting preventing portion for preventing the cassette 2 from being set in a state other than a predetermined state. The predetermined state is a state wherein the cassette 2 is set with a predetermined orientation and in predetermined position for example on a carrying part for carrying the cassettes 2.

Figure 6:
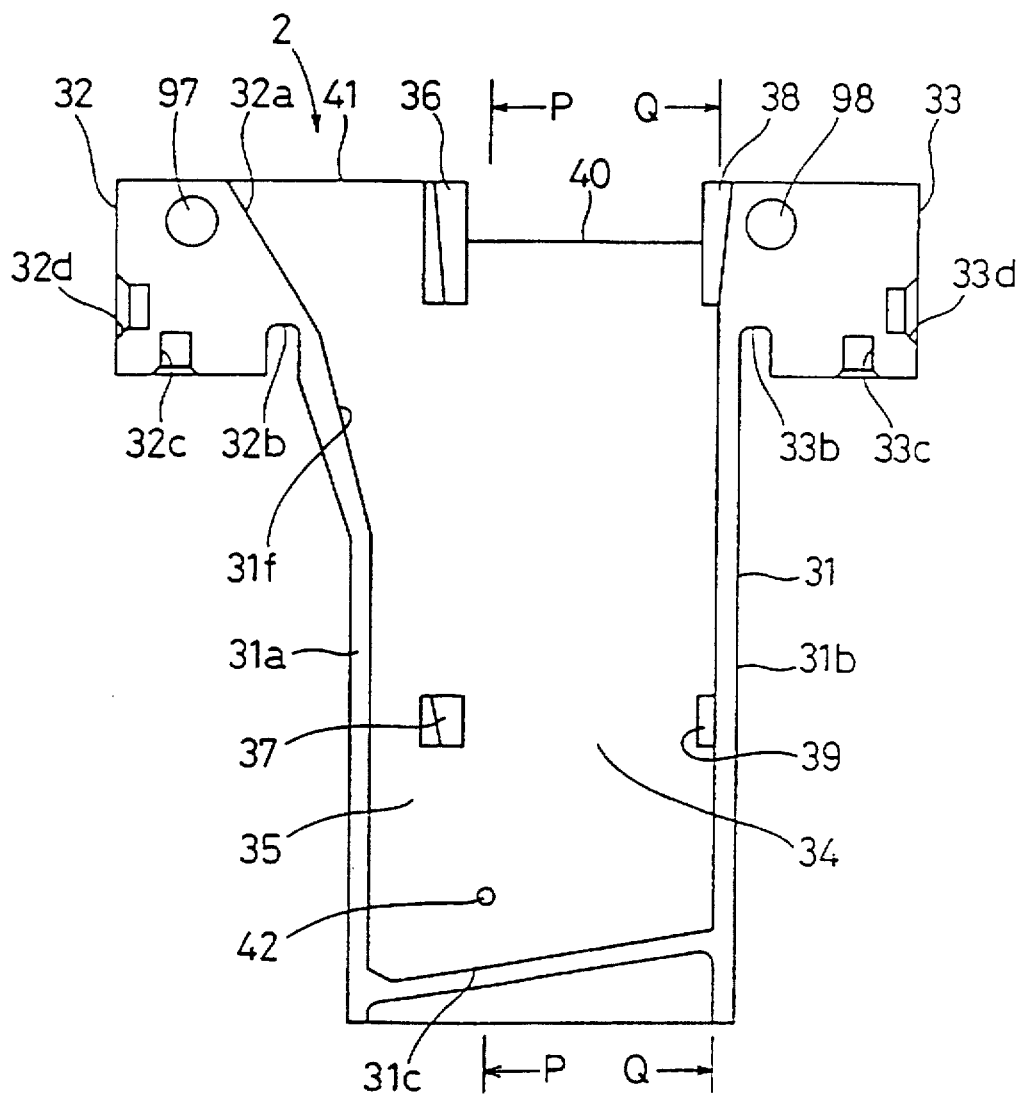
FIG. 6 is a rear view of a slide glass holding cassette of the automatic sample preparing apparatus of FIG. 1.
Figure 7:
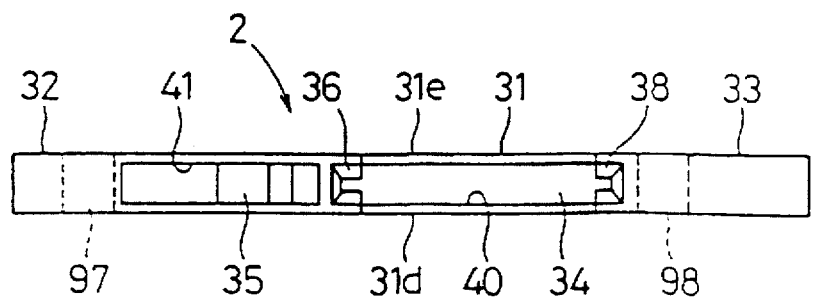
FIG. 7 is a plan view of the cassette of FIG. 6.

That is, as shown in FIG. 6, whereas on the left side of the cassette 2 the downwardly sloping portion 31f is provided between the left side hanging support part 32 and the vertical left side wall 31a, on the right side of the cassette 2 the right side wall 31b is vertical all the way up to the right side hanging support part 33. In other words, the holding part 31 of the cassette 2 is left-right asymmetric. Therefore, as shown in FIG. 12, if a reverse-setting preventing member 44 having a predetermined vertical cross-sectional shape is disposed along one side wall 43a of a table 43 U-shaped in vertical cross-section for setting empty cassettes 2 in, the cassettes 2 can be correctly set in the table 43 with a predetermined orientation.

Figure 12:
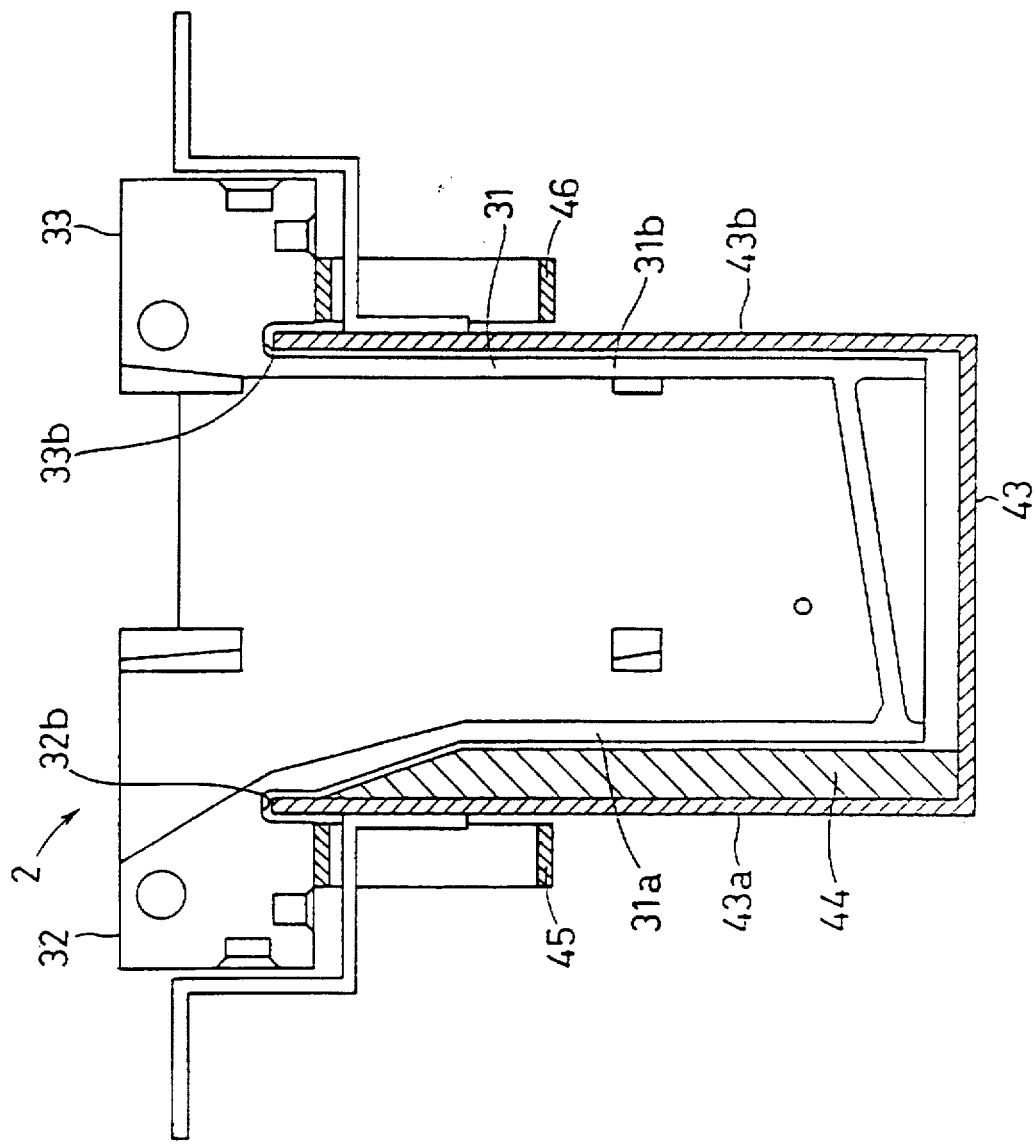
FIG. 12 is a rear view showing the cassette of FIG. 6 correctly set in a table and being carried by a carrying belt.

In FIG. 12, 45 and 46 are a pair of carrying belts for carrying cassettes 2 hanging vertically thereon by the hanging support parts 32 and 33. Also, 32b and 33b are guide grooves provided in the lower surfaces of the hanging support parts 32 and 33. When the cassette 2 is supported and carried by the carrying belts 45 and 46, the upper edges of the side walls 43a and 43b of the table 43 fit into the guide grooves 32b and 33b.

Figure 8:
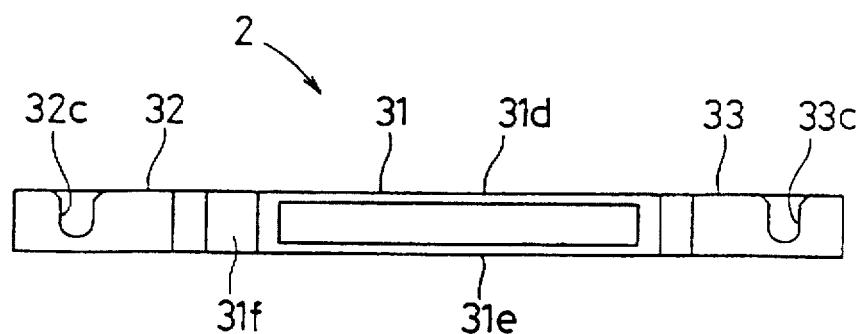
FIG. 8 is a bottom view of the cassette of FIG. 6.
Figure 9:
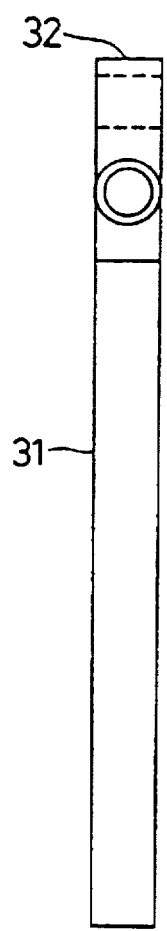
FIG. 9 is a side view of the cassette of FIG. 6.
Figure 10:
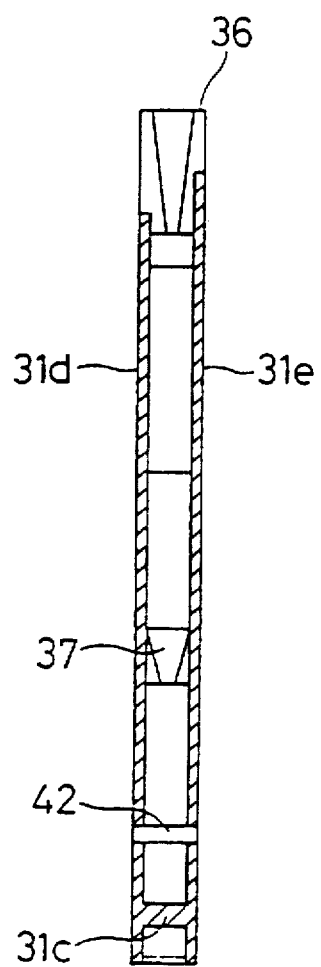
FIG. 10 is a sectional view on the line P—P in FIG. 6.
Figure 11:
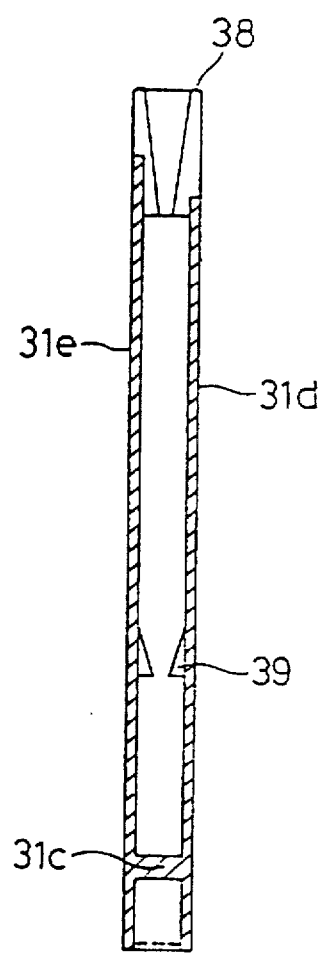
FIG. 11 is a sectional view on the line Q—Q in FIG. 6.

As shown in FIG. 6 and FIG. 8, concave portions 32c and 33c opening to the front and downward are provided in the two hanging support parts 32 and 33 respectively of the cassette 2. These concave portions 32c and 33c are for cassette releasing stoppers, which will be further discussed later, to fit into. Also, attraction members 97 and 98, which are attracted by magnets, are embedded in the two hanging support parts 32 and 33 respectively. These attraction members 97 and 98 combined with magnets are for correctly carrying out positioning of the cassette 2. A middle left guide may be further provided between the upper left guide 36 and the lower left guide 37. In this case, because the main space 34 and the auxiliary space 35 are divided by the upper left guide 36, the lower left guide 37 and the middle left guide, an effect of drying the slide glass 10, which will be further discussed later, can be improved.

Next, the overall operation of this automatic sample preparing apparatus D will be explained along with the detailed construction of the different parts of the apparatus with reference to the flow charts of FIG. 13 through FIG. 15.

Figure 13:
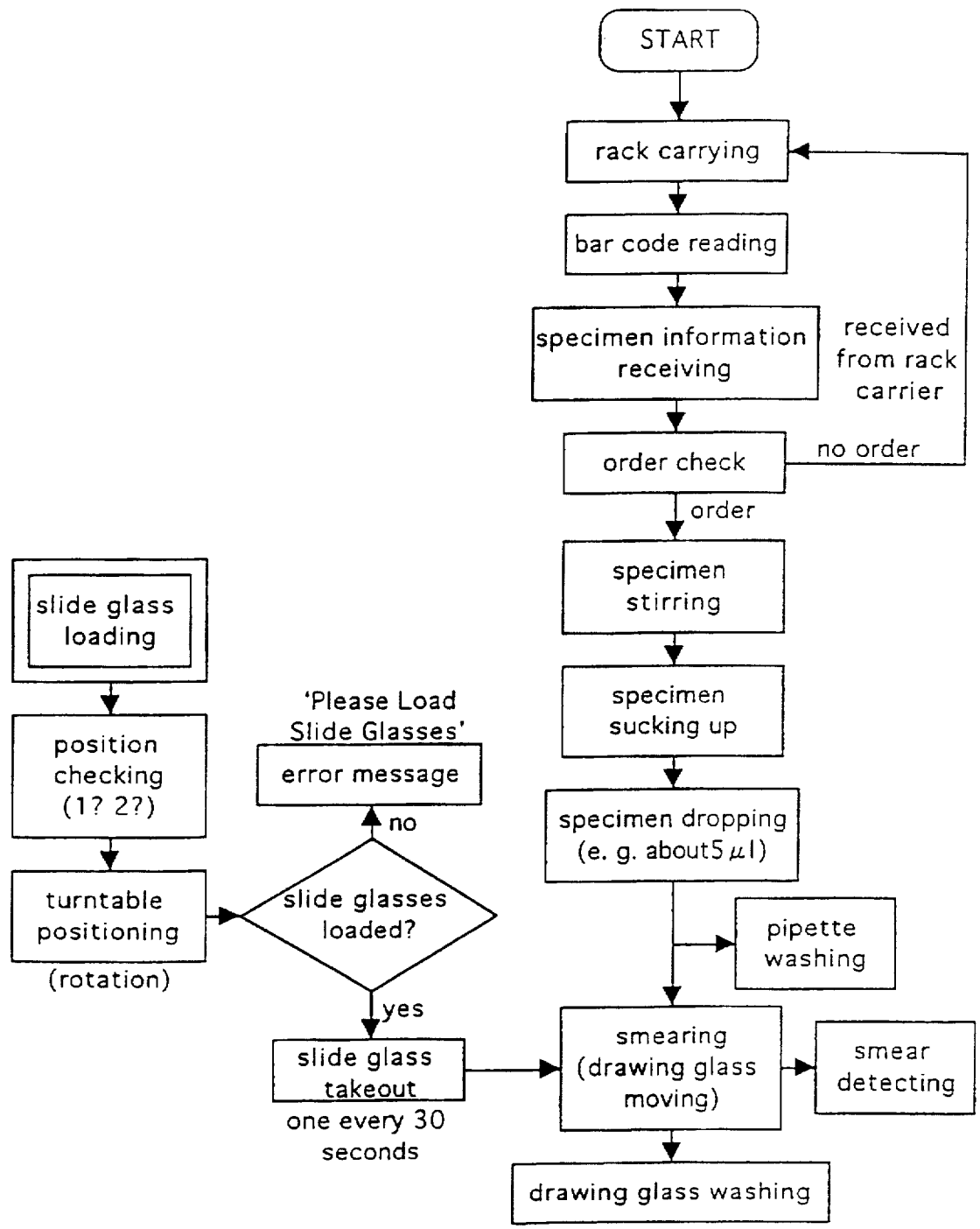
FIG. 13 is a flow chart showing the operation of the automatic sample preparing apparatus of FIG. 1 from loading of slide glasses to smearing treatment.

Referring to FIG. 13, a specimen vessel containing a blood specimen is affixed with a bar code label showing a specimen number, the date, a receipt number and a name, etc, and placed in a specimen holding rack. This rack is carried (rack carrying) by a rack carrier and stops in front of the automatic sample preparing apparatus D. Then, the bar code on the bar code label affixed to the specimen vessel is read by a bar code reader. Specimen information is then received from the rack carrier and whether or not there is an order is checked. Here, when there is no order, the process returns to rack carrying and the rack is carried. When there is an order, the specimen in the specimen vessel is stirred and then sucked up by a pipette 47b attached to an arm 47a of a blood charging mechanism 47.

The slide glass 10 is taken out of the cassette 12 and carried to a predetermined position for smearing as shown in FIG. 3 through FIG. 5, but before this a process shown in FIG. 13 is carried out. That is, it is checked whether the turntable 11 is in 'position 1' or 'position 2' (position checking) and according to the result of this check the turntable 11 is rotated clockwise or counterclockwise as necessary to bring it into the required position (turntable 11 positioning).

Next, it is determined whether there are any slide glasses 10 in the respective cassette 12, and when there are no slide glasses 10 an error message, 'Please Load Slide Glasses', is displayed. When there are slide glasses 10 in the cassette 12, a slide glass 10 is taken out of the cassette 12 by the method described above. This taking out is performed at a rate of one slide glass 10 every 30 seconds.

About 5 microliters of specimen sucked up by the pipette 47b is dropped onto this slide glass 10. This pipette 47b is then washed in a pipette washing tank 48.

Next, the specimen thus dripped onto the slide glass 10 is smeared by a smearing mechanism 49 using a wedge method in the first predetermined position of the smearing part 1. That is, smearing is carried out by a drawing glass 50 disposed in the first predetermined position being moved in the length direction of the slide glass 10 in abutment therewith. When smearing is finished the drawing glass 50 is immersed for a predetermined period in a drawing glass washing tank 51 containing a washing liquid for removing oil and proteins and then lifted out and cleaned with a nozzle.

After that, the quality of the smeared state of the specimen on the slide glass 10 is detected by a smear checking means 52. That is, the slide glass 10 after smearing passes between a pair of optical devices (a light-receiving device and a light-emitting device) disposed above and below the slide glass 10, the light transmittance at each of three places (on a straight line parallel with the short sides of the slide glass 10) near the middle of the slide glass 10 is measured and a prescribed determination is made on the basis of these light transmittances. As shown in FIG. 14, when the smear is no good an error message is displayed and when the smear is good the slide glass 10 is printed on by a dot impact type printer 53 in the second predetermined position. That is, the specimen number, the date, the receipt number and the name and the like read by the above-mentioned bar code reader are printed on the frosted portion of the slide glass 10.

The printed slide glass 10 is then forcibly dried by a drying fan 54 disposed on the right side of the second predetermined position and a drying fan 55 disposed on the right side of a third predetermined position in front of the second predetermined position (a loading-standby position which will be further discussed later).

The slide glass 10 moves horizontally to the right from the first predetermined position to the second predetermined position and moves horizontally forward from the second predetermined position to the third predetermined position, and the following means are provided to detect this horizontally movement of the slide glass 10. That is, a pair of light transmittance sensors with slits are provided in front of and behind the horizontal slide glass 10 between the first predetermined position and the second predetermined position and a pair of light transmittance sensors with slits are provided to the right side and the left side of the horizontal slide glass 10 between the second predetermined position and the third predetermined position.

The height dimension of the light-receiving side slits in these two sets of light transmittance sensors for detecting the movement of the slide glass 10 is set to less than the thickness of the slide glass 10. Also, the light-emitting side uses a pulse current in order to obtain an ample light intensity. With these two sets of sensors it is possible to detect the slide glass 10 moving horizontally even if there is a moving mechanism above or below the slide glass 10.

In FIG. 2, an empty cassette 2 supported hanging vertically from the cassette feed belt 3a of the carrying part 3 and carried forward (in the direction of the arrow) thereby is held in this vertical state by a cassette holding and transferring member 56 when it reaches the front end of the cassette feed belt 3a. That is, the cassette holding and transferring member 56 has a left-right pair of inwardly and outwardly pivotable holding arms 56a, and these holding arms 56a hold the hanging support parts 32 and 33 of the cassette 2 by pivoting inward from their outer positions. Engaging holes 32d and 33d shown in FIG. 6 are for engaging claws of the holding arms 56a to fit into and engage with at this time. The cassette holding and transferring member 56 also has a stopping mechanism for temporarily stopping cassettes 2 on the cassette crossfeed belt 3b of the carrying part 3 one at a time.

The cassette 2 thus held in a vertical state is moved by the cassette holding and transferring member 56 to the left and is stopped in front of the third predetermined position or holding standby position. The slide glass 10 having been carried to the third predetermined position is loaded from this position into the cassette 2 by the operation of the loading part 4 and the cassette holding and transferring member 56. The method of this loading will now be described.

Figure 16:
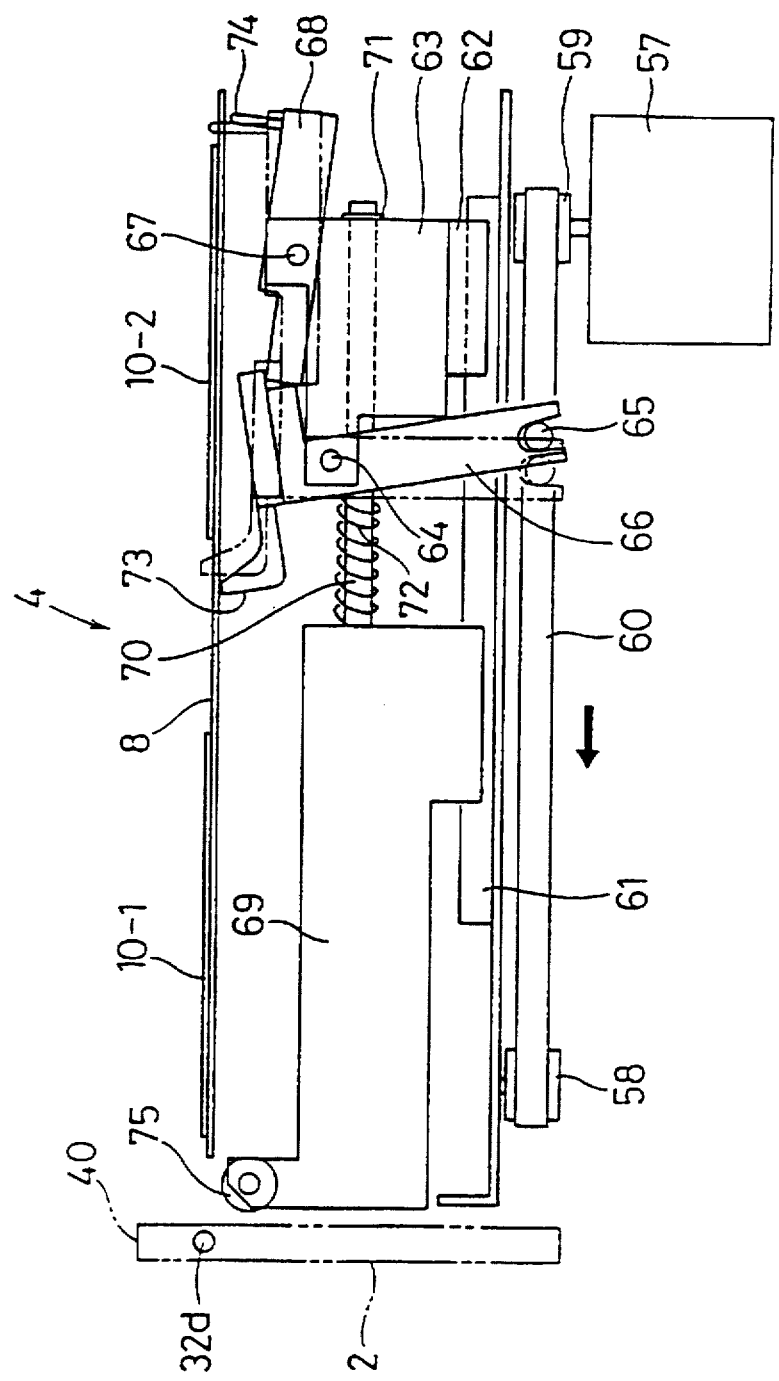
FIG. 16 is a side view showing the state before a slide glass is loaded into a cassette by a loading part in the automatic sample preparing apparatus of FIG. 1.

The left side of FIG. 16 shows the front part of the loading part 4 and the right side shows the rear part of the loading part 4. Referring to FIG. 16, the loading part 4 comprises a set of two slide glass holding parts 7 and 8 (see FIG. 2) disposed extending in the front-rear direction horizontally and in parallel with each other which support and hold the slide glass 10, a motor 57 serving as a drive source capable of rotating in forward and reverse directions, front and rear pulleys 58 and 59 and a belt 60 strung horizontally around these pulleys 58 and 59 and driven to move forward and backward by the motor 57. The loading part 4 also has a guide rail 61 disposed horizontally above the belt 60, a slider 62 which moves forward and backward guided by the guide rail 61, an arm supporting member 63 mounted on the upper surface of the guide rail 61, a first arm 66 pivotally supported by a supporting shaft 64 mounted on a portion of the arm supporting member 63 projecting forward from the upper part of the front end thereof and a supporting shaft 65 provided on the belt 60, a second arm 68 pivotally supported by a supporting shaft 67 mounted on a portion of the arm supporting member 63 projecting upward from the upper part of the rear end thereof, a cassette pivoting member 69 slidably mounted on the guide rail 61 in front of the arm supporting member 63 and a connecting bar 70 connecting the arm supporting member 63 to the cassette pivoting member 69.

The connecting bar 70 fits slidably in an insertion hole provided passing through the arm supporting member 63 from front to rear; its front end is fixed to the rear surface of the cassette pivoting member 69, and a retainer 71 is attached to its rear end. A coil spring 72 is fitted on the connecting bar 70 between the arm supporting member 63 and the cassette pivoting member 69 and urges the members 63 and 69 away from each other so that the rear surface of the arm supporting member 63 abuts with the retainer 71.

The first arm 66 is pivotable about the supporting shaft 64 and is provided at the front of its upper end with an upwardly projecting first head 73. The first head 73 can project above and sink below the two slide glass holding parts 7 and 8 between the two slide glass holding parts 7 and 8. The second arm 68 is pivotable about the supporting shaft 67 and is provided on the upper part of its rear end with an upwardly projecting second head 74. The second head 74 can also project above and sink below the two slide glass holding parts 7 and 8. The second arm 68 is caused to pivot by pivoting of the first arm 66.

A roller 75 is attached to the upper part of the front end of the cassette pivoting member 69. When the cassette pivoting member 69 moves forward, the roller 75 abuts with the rear surface of the vertically oriented cassette 2 and then causes the cassette 2 to pivot forward and upward about the engaging holes 32d and 33d in the cassette 2. The external diameter of the roller 75 and the height at which it is mounted are set so that when the cassette 2 has been pivoted forward and upward as far as possible by the cassette pivoting member 69 and the roller 75 the cassette 2 is horizontal.

In FIG. 16, the solid lines show the positions (the initial position) of the various members before the start of operation of the loading part 4. Referring to FIG. 16, when the motor 57 rotates forward and the belt 60 moves in the direction of the arrow and the supporting shaft 65 moves from the position in which it is shown with a solid line to the position in which it is shown with a two-dot chain line, the first arm 66 pivots clockwise about the supporting shaft 64 and becomes vertical as shown with two-dot chain lines. Together with this, the first head 73 also pivots clockwise about the supporting shaft 64 and is lifted up as shown with two-dot chain lines.

When this happens, the rear part of the upper end of the first arm 66 causes the second arm 68 to pivot counterclockwise about the supporting shaft 67 and become horizontal as shown with two-dot chain lines, and the second head 74 is lifted up.

When the belt 60 moves further in the direction of the arrow, the arm supporting member 63 moves forward together with the vertical first arm 66 and the horizontal second arm 68. Together with this, the first head 73 pushes the rear end of the slide glass 10 (a first slide glass 10-1) in the loading-standby position and the second head 74 pushes the rear end of the slide glass 10 (a second slide glass 10-2) immediately behind the first slide glass 10-1 and the slide glasses 10-1 and 10-2 are moved forward.

At this time, the arm supporting member 63 pushes the cassette pivoting member 69 by way of the coil spring 72 as it moves forward. The roller 75 abuts with the rear surface of the vertically oriented cassette 2.

Figure 17:
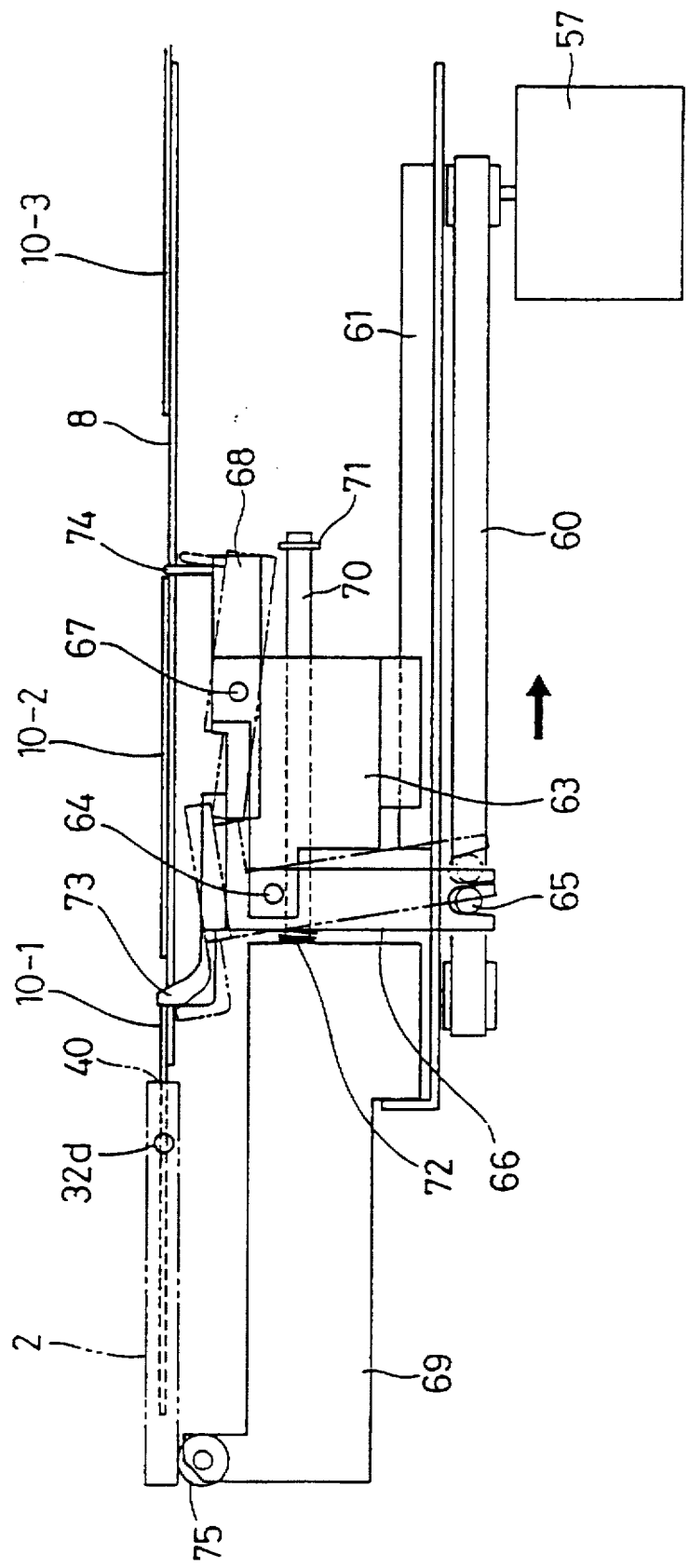
FIG. 17 is a side view showing a state after a slide glass is loaded into a cassette by the loading part of FIG. 16.

Next, as shown in FIG. 17, the roller 75 pivots the cassette 2 forward as far as possible (in terms of angle, 90°) about the engaging holes 32d and 33d in the cassette 2. The first slide glass 10-1 pushed by the first head 73 is then inserted into the now horizontal cassette 2 through the slide glass receiving hole 40 thereof. At this time, the arm supporting member 63 and the cassette pivoting member 69 move as far forward as they can go. The solid lines in FIG. 17 show the positions (final positions) of the various members at this time.

The final position of the second slide glass 10-2 in FIG. 17 is the same as the position of the first slide glass 10-1 in its initial position shown in FIG. 16. Also, a third slide glass 10-3 following the second slide glass 10-2 has been carried to immediately behind the second slide glass 10-2 in this final position.

When from the final position shown in FIG. 17 the motor 57 rotates in reverse and the belt 60 moves in the direction of the arrow and the supporting shaft 65 moves from the position in which it is shown with a solid line to the position in which it is shown with a two-dot chain line, the first arm 66 pivots counterclockwise about the supporting shaft 64 and inclines as shown with two-dot chain lines. Together with this, the first head 73 also pivots counterclockwise about the supporting shaft 64 and the first head 19a descends as shown with two-dot chain lines.

When this happens, the rear part of the upper end of the first arm 66 is lifted up and the second arm 68 pivots clockwise about the supporting shaft 67, and the second head 74 descends as shown with two-dot chain lines. Then, when the belt 60 moves further in the direction of the arrow, the arm supporting member 63 moves backward together with the first arm 66 and the second arm 68 and the rear surface of the arm supporting member 63 abuts with the retainer 71 of the connecting bar 70. When the arm supporting member 63 moves further backward, the cassette pivoting member 69 is also moved backward by the connecting bar 70 and returns to its initial position.

When returning to their initial positions, because the first head 19a and the second head 74 are lowered, as shown with two-dot chain lines in FIG. 17, they do not interfere with the second slide glass 10-2 or the third slide glass 10-3.

In this way, the slide glass 10 carried to the third predetermined position is loaded into the cassette 2 from this position by the operation of the loading part 4 and the cassette holding and transferring member 56. After the cassette 2 having received the slide glass 10 is brought to the vertical by the cassette holding and transferring member 56 it is placed on the cassette crossfeed belt 3b by the cassette holding and transferring member 56 and carried to the left by the cassette crossfeed belt 3b until it stops in front of the pusher 76.

The pusher 76 pushes the cassettes 2 arriving in front of it one at a time onto a double cassette carrying belt 5a in the dyeing part 5. The cassettes 2 are thereby fed one by one into the dyeing part 5 by the pusher 76.

A cassette interrupt supply member 77 is provided to the right of the pusher 76. It is possible to load an interrupt cassette containing a slide glass to be dyed into the cassette interrupt supply member 77 and place it on the cassette crossfeed belt 3b whenever desired, separately from cassettes 2 carried to the left on the cassette crossfeed belt 3b.

Figure 14:
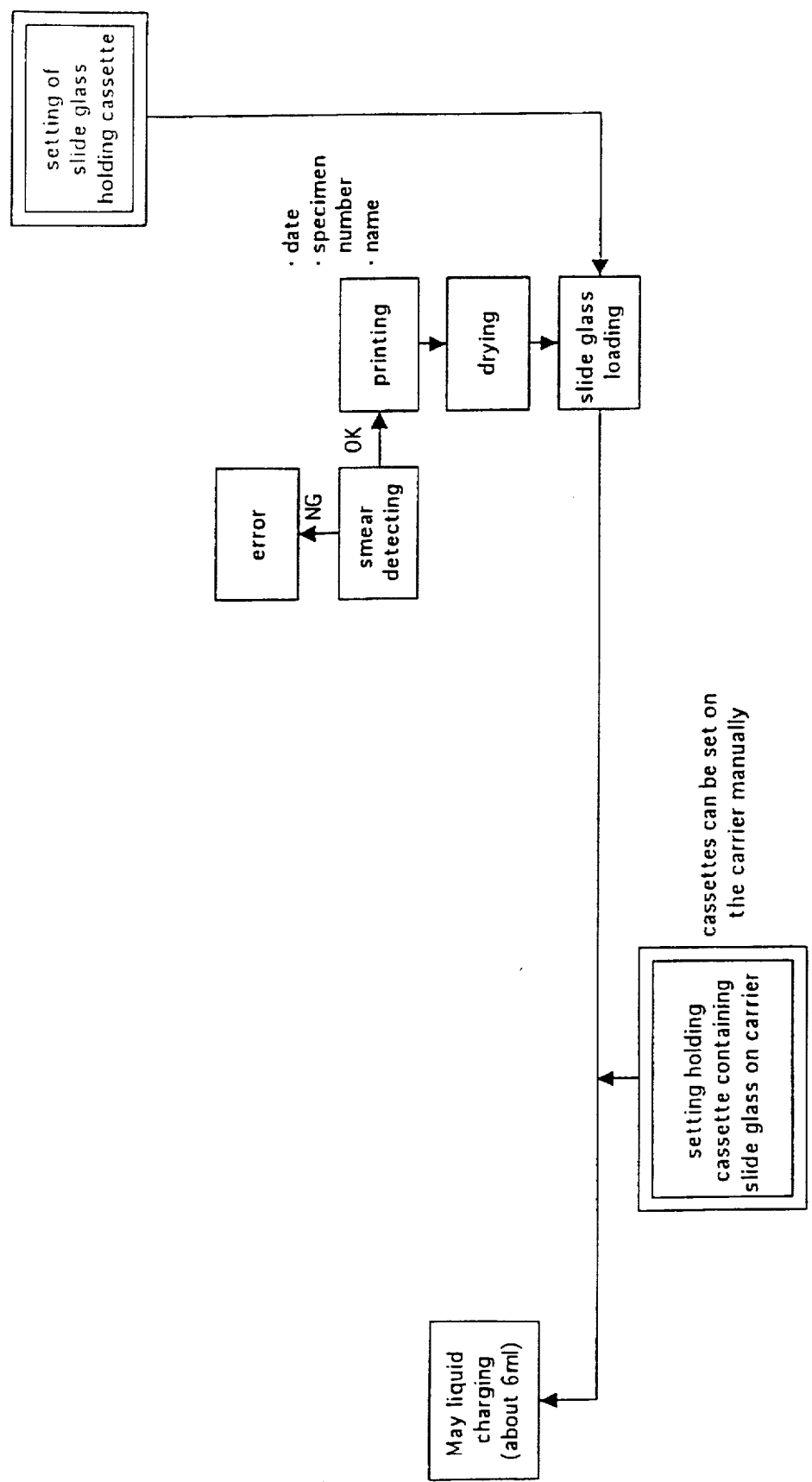
FIG. 14 is a flow chart showing the operation of the automatic sample preparing apparatus of FIG. 1 from detection after smearing to loading of a slide glass into a cassette.
Figure 15:
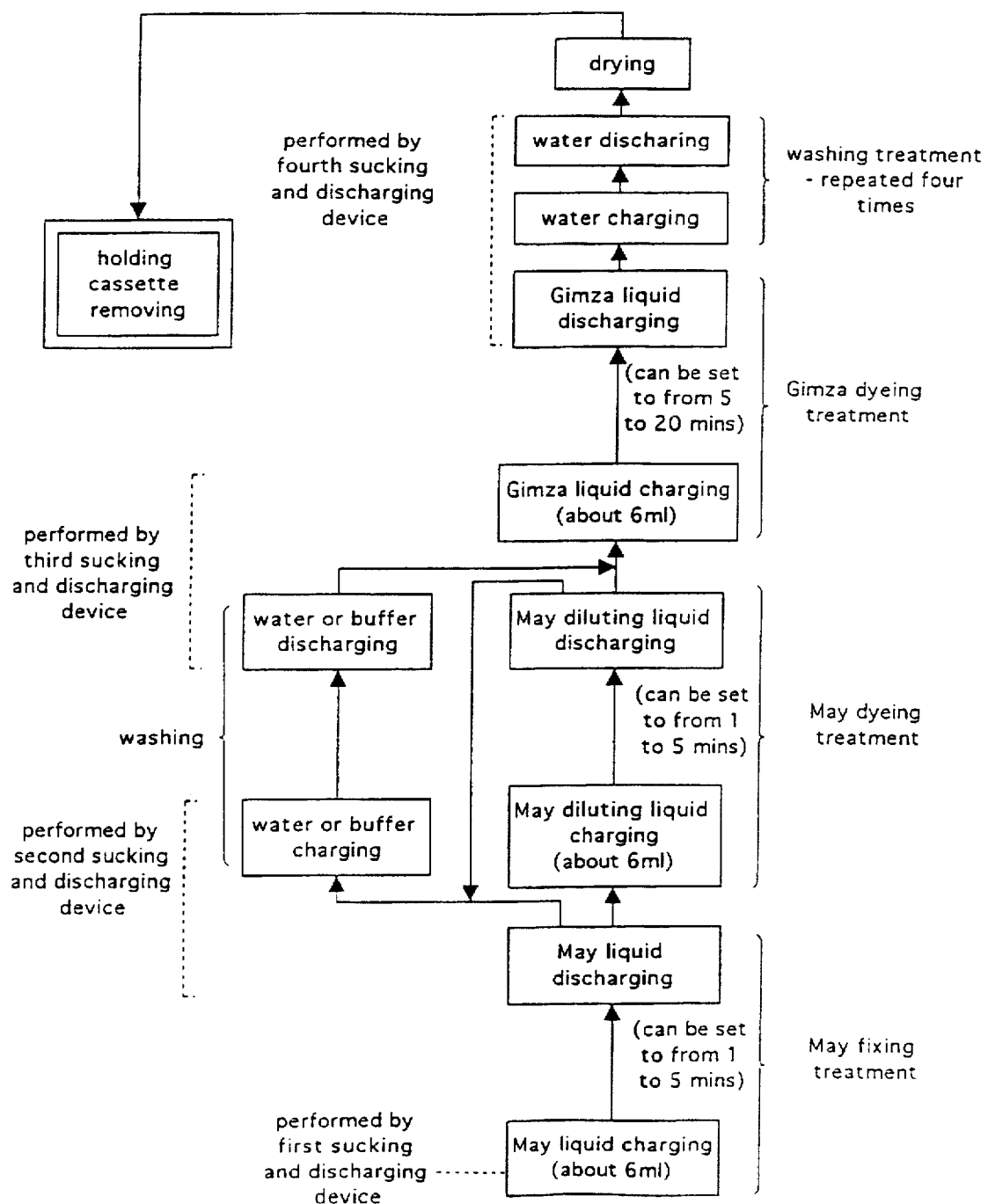
FIG. 15 is a flow chart showing the overall dyeing treatment operation of the automatic sample preparing apparatus of FIG. 1.

As shown in FIG. 14, about 6 milliliters of May Gr ünwald stain liquid (hereinafter abbreviated to 'May liquid') for dyeing is charged into the inside of the cassette 2 containing the slide glass 10 and fed into the dyeing part 5. This starts a dyeing process which will now be explained in detail.

Figure 18:
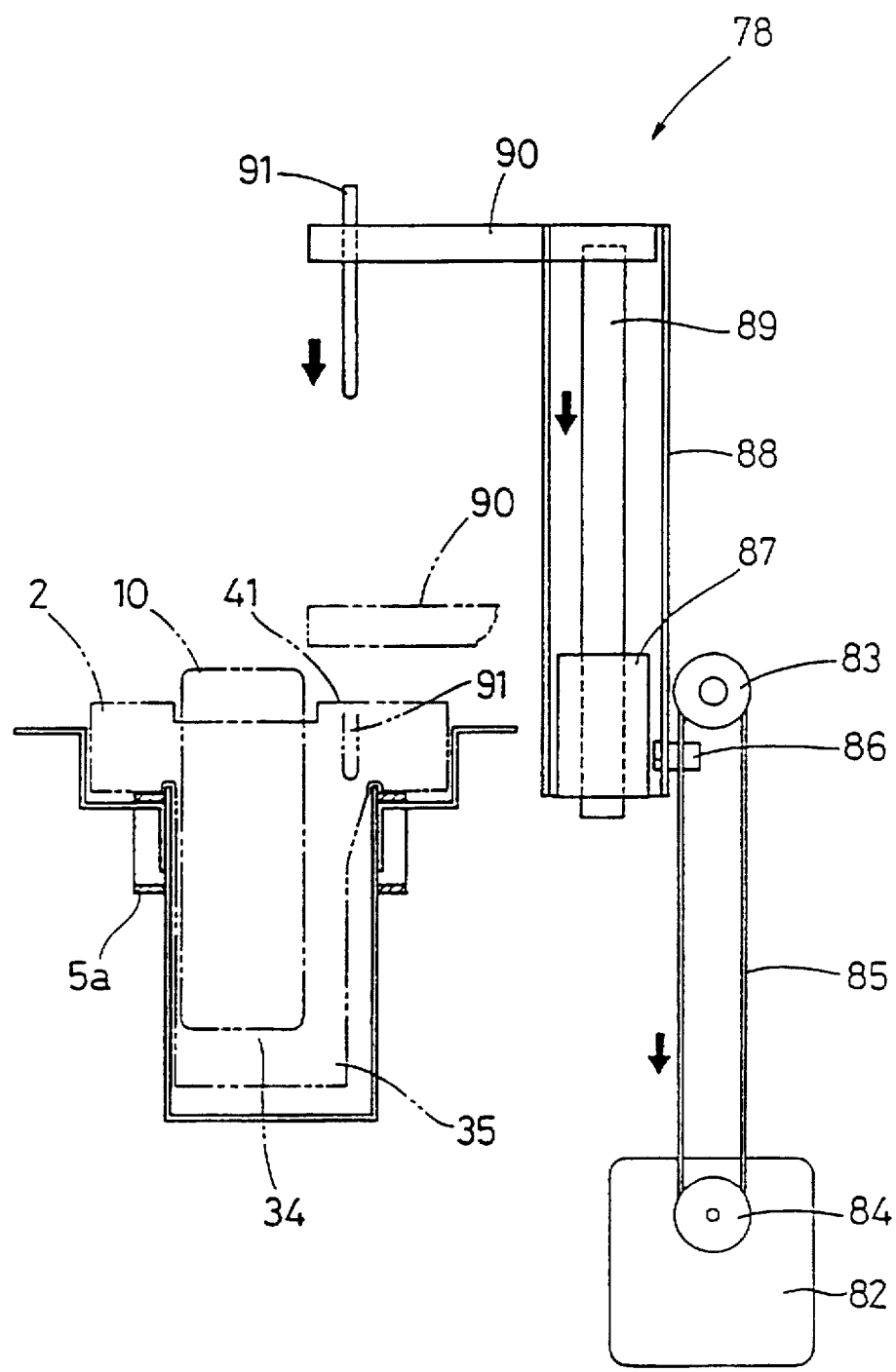
FIG. 18 is a front view showing a first sucking and discharging device of a dyeing part of the automatic sample preparing apparatus of FIG. 1.

That is, the dyeing part 5 comprises first to fourth sucking and discharging devices 78, 79, 80 and 81 disposed in this order from the front to the rear of the dyeing part 5, as shown in FIG. 1. The first sucking and discharging device 78, as shown in FIG. 18, comprises a motor 82 serving as a drive source and capable of rotating in forward and reverse directions, upper and lower pulleys 83 and 84, a belt 85 which is strung vertically around the pulleys 83 and 84 and moves up and down driven by the motor 82, a connecting member 86 attached to the belt 85, a guide member 87 mounted to the left of the upper pulley 83 and having a vertical guide groove, a cylindrical cover 88 vertically disposed covering the guide member 87 and attached to the connecting member 86, a slide rod 89 vertically disposed inside the cover 88 and fitted slidably in the guide groove of the guide member 87, a horizontal arm 90 attached to the top end of the slide rod 89 and the top end of the cover 88 and projecting to the left and a first pipette 91 for charging vertically passing through a pipette hole provided in the arm 90 near the left end thereof.

The cassette 2 pushed onto the cassette carrying belt 5a of the dyeing part 5 by the pusher 76 is carried as far as to the left of the first sucking and discharging device 78 and then temporarily stops there. At this time, the pipette insertion opening 41 of the cassette 2 is positioned directly underneath the first pipette 91 of the first sucking and discharging device 78. When the cassette 2 temporarily stops to the left of the first sucking and discharging device 78, the motor 82 shown in FIG. 18 rotates forward and the belt 85 moves in the direction shown with an arrow, and the slide rod 89 is moved in the direction of the arrow by way of the connecting member 86 integral with the belt 85 and the cover 88. Together with this the arm 90 descends to the position in which it is shown with two-dot chain lines. At this time, the first pipette 91 has been inserted into the pipette insertion opening 41 of the cassette 2 and descended to the position in which it is shown with two-dot chain lines.

About 6 milliliters of May liquid supplied through a dyeing liquid supply tube (not shown in the drawings) is charged from the first pipette 91 into the auxiliary space 35 of the cassette 2. The charged May liquid also flows into the main space 34 and immerses the smeared part of the slide glass 10 in the main space 34. Next, the cassette 2 is carried to the left of the second sucking and discharging device 79 by the cassette carrying belt 5a and then stopped there.

Figure 19:
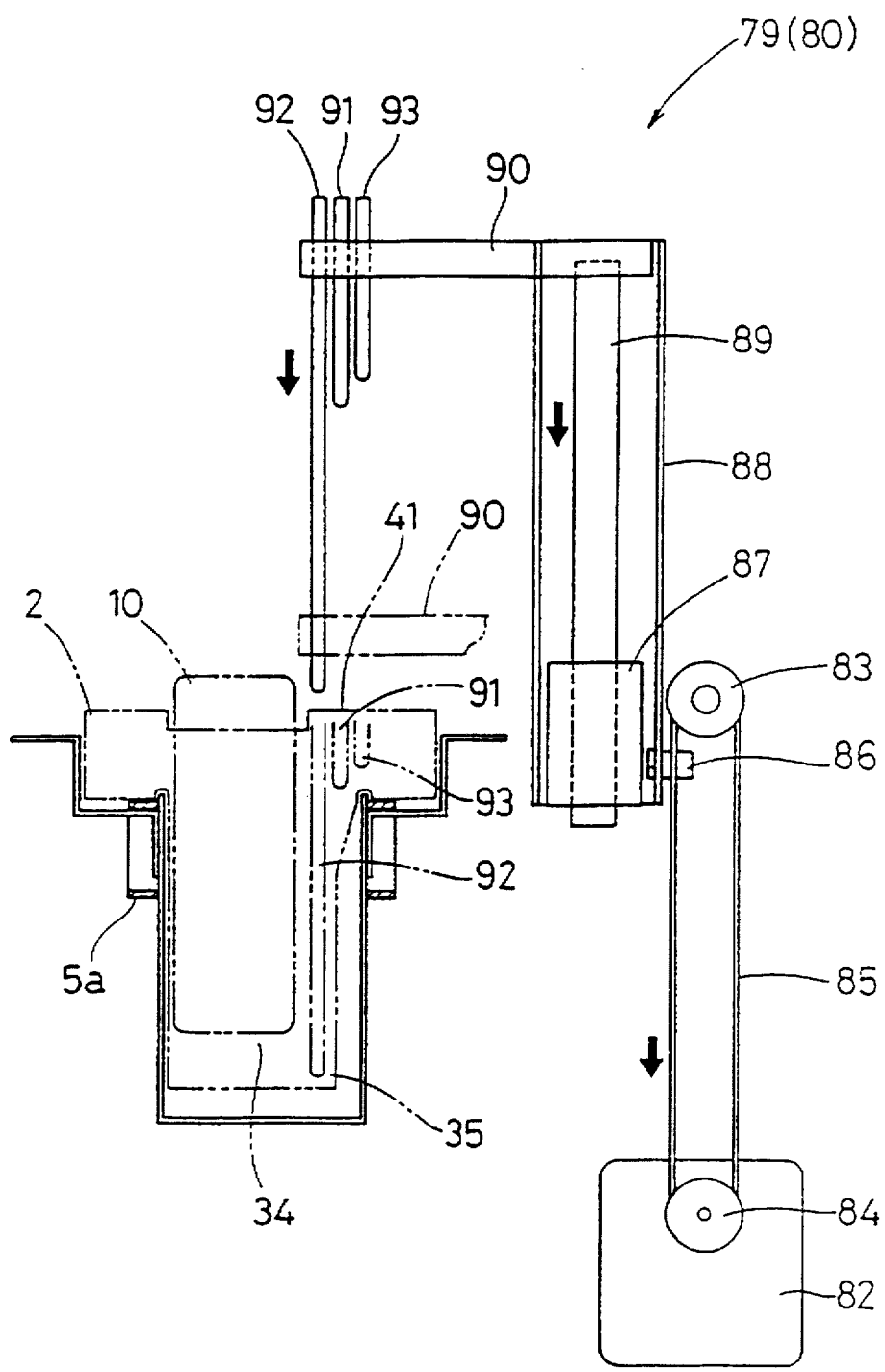
FIG. 19 is a front view showing a second sucking and discharging device and a third sucking and discharging device of the dyeing part of FIG. 18.

The second sucking and discharging device 79 is of the construction shown in FIG. 19. That is, in addition to the various constituent parts of the first sucking and discharging device 78 the second sucking and discharging device 79 has a second pipette 92 for sucking passing vertically through a pipette hole provided in the arm 90 to the left of the first pipette 91 and a third pipette 93 for charging passing through a pipette hole provided to the right of the first pipette 91. The first to third pipettes 91, 92 and 93 are disposed in a line.

The pipette insertion opening 41 of the cassette 2 having been carried to the left of the second sucking and discharging device 79 and stopped there is positioned directly underneath the first to third pipettes 91, 92 and 93.

When the cassette 2 stops on the left of the second sucking and discharging device 79, in the same way as in the first sucking and discharging device 78 the arm 90 descends to the position in which it is shown with two-dot chain lines. At this time, the first to third pipettes 91, 92 and 93 are inserted into the pipette insertion opening 41 of the cassette 2 and descend to the positions shown with two-dot chain lines.

In this position, the May liquid inside the cassette 2 is all sucked up by the second pipette 92 of the second sucking and discharging device 79 and discharged (May liquid discharging) through a liquid discharge tube (not shown in the drawings). As shown in FIG. 15, the time from the May liquid charging to the May liquid discharging, that is, the May fixing treatment time, can be freely set to from 1 to 5 minutes.

To prevent May liquid from adhering to the outside surface of the second pipette 92 and the second pipette 92 consequently becoming dirty, the May liquid discharging is controlled so that the sucking and discharging operation is carried out while the second pipette 92 is descending. That is, if the speed of descent of the second pipette 92 is written $v$ cm/s, the suction discharge rate of the second pipette 92 is written $v$ cm$^3$/s and the area of the May liquid inside the cassette 2 as seen from above at a given time (the internal cross-sectional area of the cassette 2 at the height of the surface of the liquid at that time) is written $S$ cm$^2$, the second pipette 92 is controlled so as to descend at a speed $v$ satisfying $v \leq V/S$. Also, new May liquid is usually used each time, but in cases such as when minimizing running costs is important it may be made possible to reuse the May liquid two or three times.

After the May fixing treatment has been finished, about 6 milliliters of May diluting liquid supplied through a dyeing liquid supply tube (not shown in the drawing) of the second sucking and discharging device 79 is charged into the auxiliary space 35 of the cassette 2 through the first pipette 91. The charged May diluting liquid also flows into the main space 34 of the cassette 2 and immerses the May fixing treated part (the smeared part) of the slide glass 10 in the main space 34. The cassette 2 is then carried to the left of the third sucking and discharging device 80 by the cassette carrying belt 5a and stopped there.

The third sucking and discharging device 80 is of the same construction as the second sucking and discharging device 79 shown in FIG. 19. When the cassette 2 stops on the left of the third sucking and discharging device 80, the arm 90 of the third sucking and discharging device 80 descends to the position shown with two-dot chain lines as in the case of the second sucking and discharging device 79. At this time, the first to third pipettes 91, 92 and 93 have been inserted into the pipette insertion opening 41 of the cassette 2 and descended to the positions shown with two-dot chain lines.

In this position, the May diluting liquid inside the cassette 2 is all sucked up by the second pipette 92 of the third sucking and discharging device 80 and discharged (May diluting liquid discharging) through a liquid discharge tube (not shown in the drawings). To prevent May diluting liquid from adhering to the outside surface of the second pipette 92 and the second pipette 92 consequently becoming dirty, the May diluting liquid discharging is controlled in the same way as in the case of the May liquid discharging (i.e. so that the second pipette 92 descends at a speed $v$ satisfying $v \leq V/S$). New May diluting liquid is usually used each time, but in cases such as when minimizing running costs is important it may be made possible to reuse the May diluting liquid two or three times. The time from the May diluting liquid charging to the May diluting liquid discharging, that is, the May dyeing treatment time, can be freely set to from 1 to 5 minutes.

To shorten the overall dyeing treatment time or reduce running costs this May dyeing treatment may be omitted and washing of the slide glass 10 carried out instead. That is, as shown in FIG. 15, washing of the slide glass 10 may be carried out by water for washing (for example ion exchange water) or a buffer (for example phosphoric acid buffer liquid) being charged into the cassette 2 after the May liquid discharging is finished from the third pipette 93 of the second sucking and discharging device 79 and this water or buffer then being discharged by the second pipette 92 of the third sucking and discharging device 80. The same washing treatment may also be carried out after the May dyeing treatment.

When the May dyeing treatment or washing treatment is finished, 6 milliliters of Gimza liquid supplied through a dyeing liquid supply tube (not shown in the drawings) of the third sucking and discharging device 80 is charged into the auxiliary space 35 of the cassette 2 from the first pipette 91 of the third sucking and discharging device 80. The charged Gimza liquid also flows into the main space 34 of the cassette 2 and immerses the May dyeing treated or washing treated part (the smeared part) of the slide glass 10 in the main space 34. The cassette 2 is then carried to the left of the fourth sucking and discharging device 81 by the cassette carrying belt 5a and stopped there.

Figure 20:
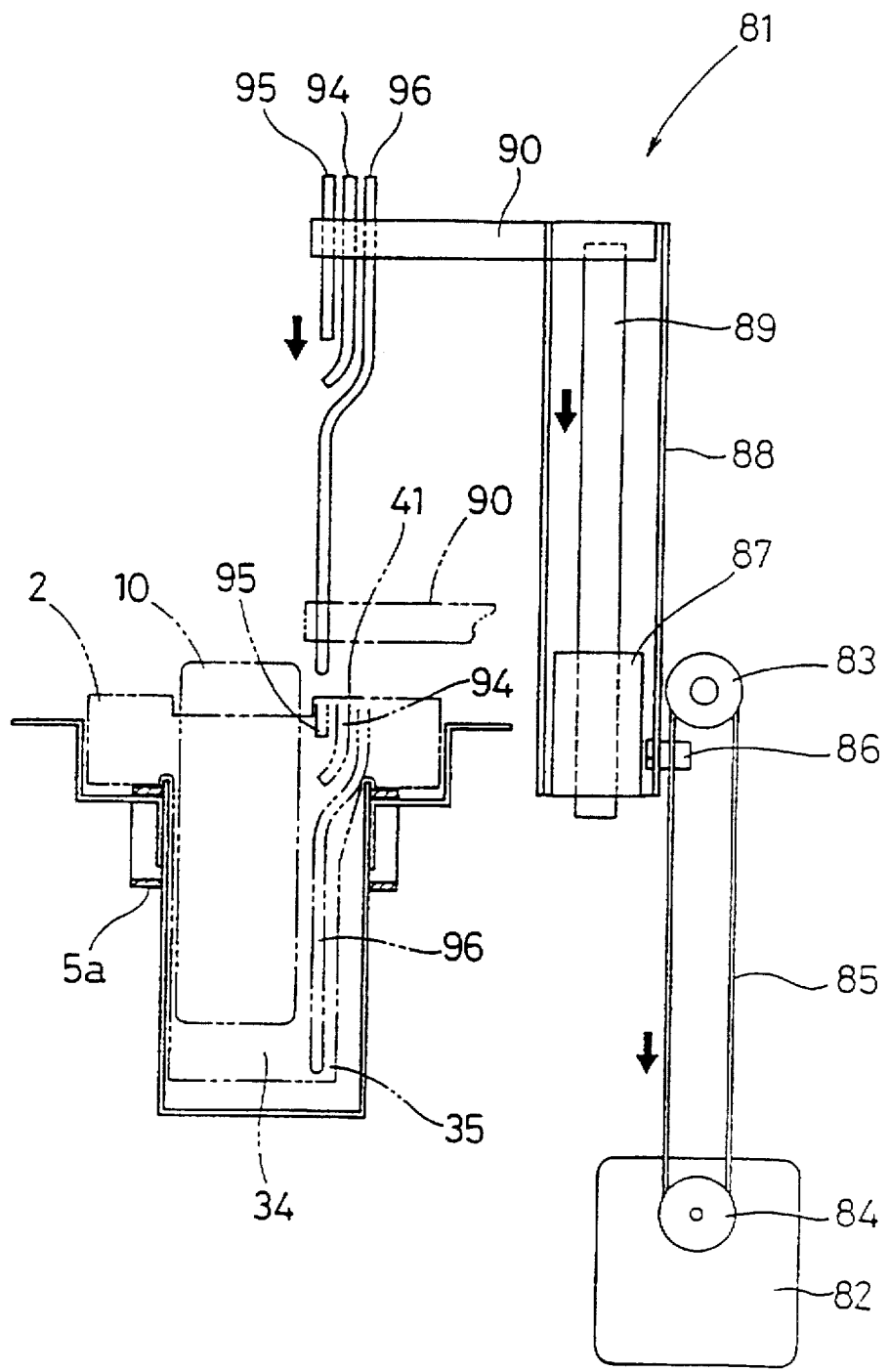
FIG. 20 is a front view showing a fourth sucking and discharging device of the dyeing part of FIG. 18.

The fourth sucking and discharging device 81 is of the construction shown in FIG. 20. That is, the fourth sucking and discharging device 81, unlike the first to third sucking and discharging devices 78, 79 and 80, has a first pipette 94 for washing water charging passing vertically through a pipette hole provided in the arm 90, a second pipette 95 for overflow prevention passing vertically through a pipette hole provided in the arm 90 to the left of the first pipette 94 and a third pipette 96 for liquid sucking passing vertically through a pipette hole provided in the arm 90 to the right of the first pipette 94. The first to third pipettes 94, 95 and 96 are disposed in a line.

The length of the first pipette 94 is substantially the same as that of the first pipettes 91 of the first to third sucking and discharging devices 78, 79 and 80, but its lower end is bent to the left. This is so that washing water charged from the first pipette 94 strikes the front side and the rear side of the slide glass 10 in the cassette 2 from the right edge of the slide glass 10. The second pipette 95 is shorter than the first pipette 94 and is straight, and to prevent washing water inside the cassette 2 from overflowing sucks up washing water inside the cassette 2 having reached a certain level. The length of the third pipette 96 is substantially the same as that of the third pipettes 93 of the first to third sucking and discharging devices 78, 79 and 80, but its middle portion is bent to the left to enable it to be inserted into the auxiliary space 35 of the cassette 2.

The pipette insertion opening 41 of the cassette 2 having been carried to the left of the fourth sucking and discharging device 81 and stopped there is positioned directly underneath the first to third pipettes 94, 95 and 96 of the fourth sucking and discharging device 81.

When the cassette 2 stops on the left of the fourth sucking and discharging device 81, as in the case of the first sucking and discharging device 78 the arm 90 descends to the position in which it is shown with two-dot chain lines. At this time, the first to third pipettes 94, 95 and 96 have been inserted into the pipette insertion opening 41 of the cassette 2 and descended to the positions in which they are shown with two-dot chain lines.

In this position, all the Gimza liquid in the cassette 2 is sucked up by the third pipette 96 and discharged (Gimza liquid discharging) through a liquid discharge tube (not shown in the drawings). As shown in FIG. 15, the time from the Gimza liquid charging to the Gixza liquid discharging, that is, the Gimza dyeing treatment time, can be set freely to from 5 to 20 minutes.

To prevent Gimza liquid from adhering to the outside surface of the third pipette 96 and the third pipette 96 consequently being dirtied, as in the case of the May diluting liquid discharging, the Ginza liquid discharging is controlled so that the third pipette 96 descends at a speed v satisfying $v \leq V/S$. Also, new Gimza liquid is usually used each time, but in cases such as when minimizing running costs is important it may be made possible to reuse the Gimza liquid two or three times.

After the Gimza dyeing treatment is finished, washing water (for example ion exchange water) supplied through a washing water supply tube (not shown in the drawings) of the fourth sucking and discharging device 81 is charged from the first pipette 94. The charged washing water fills the main space 34 and the auxiliary space 35 of the cassette 2 and washes the Gimza dyeing treated part of the slide glass 10 (the smeared part). The washing water in the main space 34 and the auxiliary space 35 is then sucked up by the third pipette 96 and discharged through a discharge tube (not shown in the drawings). This charging and suction discharging of washing water is repeated four times and the water washing treatment is concluded.

To temporarily stop the cassette 2 to the left of each of the above-mentioned first to fourth sucking and discharging devices 78, 79, 80 and 81, a pair of cassette stopping stoppers (not shown in the drawings) and a pair of cassette releasing stoppers (not shown in the drawings) are provided one behind the other. These stoppers operate mutually oppositely. That is, when the front stoppers (the stopping stoppers) are protruded above the upper surface of the cassette carrying belt 5a the rear stoppers (the releasing stoppers) are withdrawn to below that surface, and when the upper ends of the releasing stoppers are protruded they fit into the concave portions 32c and 33c in the hanging support parts 32 and 33 of the cassette 2 carried on the cassette carrying belt 5a.

The cassette 2 after the water washing treatment is finished is carried by the cassette carrying belt 5a to the left of a drying fan 99 disposed behind the fourth sucking and discharging device 81, and there the slide glass 10 inside the cassette 2 is forcibly dried by the drying fan 99. This drying time can be freely set to from 1 to 15 minutes. At this time, because the drying wind is blown into the auxiliary space 35 through the pipette insertion opening 41 of the cassette 2 and passes through the main space 34 and out through the slide glass receiving hole 40, the slide glass 10 is efficiently dried.

The cassette 2 containing the dried slide glass 10 is fed out from the cassette carrying belt 5a of the dyeing part 5 to a cassette feed-out/feed-in mechanism 100. The cassette feed-out/feed-in mechanism 100 is disposed behind the dyeing part 5 and the storing part 6 and is connected to both, and operates to move cassettes 2 fed out from the cassette carrying belt 5a to the left one at a time and then load those cassettes 2 onto a double cassette carrying belt 6a of the storing part 6.

Cassettes 2 loaded onto the cassette carrying belt 6a of the storing part 6 by the cassette feed-out/feed-in mechanism 100 are carried forward by the cassette carrying belt 6a. Cassettes 2 having been carried to the front end of the storing part 6 abut with a front wall 6b of the storing part 6 and stop. The cassette carrying belt 6a is normally moving, and cassettes 2 coming in afterwards abut with the stopped cassette 2 in front of them.

In this way, a predetermined number of cassettes 2 are collected on the cassette carrying belt 6a of the storing part 6. The predetermined number of collected cassettes 2 are then taken out of the storing part 6.

Because an automatic sample preparing apparatus according to the invention has the construction described above it provides the following clear benefits:

That is, an automatic sample preparation apparatus according to the invention comprises a smearing part for smearing blood on a slide glass for a sample, a carrying part for having removably set thereon and carrying one or more slide glass holding cassettes each having a holding part capable of holding a slide glass and a liquid, a loading part for loading slide glasses into the cassettes one by one, and a dyeing part for supplying dyeing liquid to the cassettes and dyeing the slide glasses after blood is smeared thereon, and as a result it is possible to automatically perform the chain of operations consisting of smearing blood on a slide glass, loading smeared slide glasses one at a time into cassettes on the carrying part and then in the dyeing part supplying dyeing liquid to the cassettes and dyeing the smears of blood on the slide glasses, and also it is possible to increase the degree of freedom of handling of the slide glasses and of control of the process.

When each slide glass holding cassette comprises hanging support parts connected to the holding part for supporting the holding part in a hanging state, by the slide glass cassettes being supported by the hanging support parts while holding a predetermined number of slide glasses and a predetermined amount of a liquid and being carried and stored, compared to a conventional case there is no wasting of dyeing liquid even when the number of samples to be dyed is small and there is the effect that the degree of freedom of handling of the slide glasses and of control of the process is high.

When the holding part of each slide glass holding cassette comprises a main space capable of holding a slide glass and a liquid, an auxiliary space for liquid supply and discharge adjacent to the main space and connected to the main space and a bottom wall provided extending across the main space and the auxiliary space and sloping downward from the main space toward the auxiliary space, in addition to the effects provided by the slide glass holding cassette mentioned above, it is easy to load a slide glass into the main space and supply and discharge dyeing liquid and washing liquid through the auxiliary space and furthermore by means of the presence of the bottom wall it is possible to prevent surface tension in gaps between the lower part of the slide glass held in the main space and the side walls of the main space from causing dyeing liquid to remain in those gaps after dyeing.

When the holding part of each slide glass holding cassette comprises positioning parts for holding a slide glass in a position on one side of the inside of the holding part, in addition to the effects of the slide glass holding cassette mentioned above, if the slide glass is held by the positioning parts in a position on one side of the inside of the holding part, supply and discharge of dyeing liquid and washing liquid and the like though the other side can be carried out easily.

When the slide glass holding cassette is provided with a mis-setting prevention part for preventing the cassette from being set other than in a predetermined state, in addition to the effects described above it becomes possible to set the cassette in a prescribed position with a prescribed orientation easily.

When the loading part comprises slide glass holding parts for holding a smeared slide glass substantially horizontally, a stopping mechanism for temporarily stopping cassettes on the carrying part one by one, a pivoting mechanism for reversibly pivoting to a substantially horizontal position a cassette temporarily stopped by the stopping mechanism and a moving and inserting mechanism for moving a smeared slide glass held by the slide glass holding part and inserting it into the cassette pivoted to a substantially horizontal position by the pivoting mechanism, in addition to the effects of the automatic sample preparation apparatus described above it is possible automatically to load smeared slide glasses into cassettes temporarily stopped on the carrying part.

When the dyeing part comprises pipettes capable of being inserted into the cassettes, in addition to the effects of the automatic sample preparation apparatus described above it is possible to carry out supply and discharge of dyeing liquid and washing liquid and the like easily by the pipettes being inserted into the cassettes.

When the automatic sample preparation apparatus further comprises a storing part for storing cassettes holding smeared slide glasses fed out from the dyeing part, it is possible to automatically perform the chain of operations consisting of smearing blood on a slide glass in the smearing part, in the loading part loading smeared slide glasses one at a time into cassettes on the carrying part and then in the dyeing part supplying dyeing liquid to the cassettes and dyeing the smears of blood on the slide glasses and then in the storing part storing cassettes containing smeared slide glasses, and also it is possible to increase the degree of freedom of handling of the slide glasses and of control of the process.

What is claimed is:

1. An automatic sample preparing apparatus comprising:
   a smearing part for smearing a sample on a slide glass;
   a carrying part for removably setting and carrying at least one cassette;
   said at least one cassette including a holding part for holding a slide glass and a liquid therein;
   a loading part for loading slide glasses into the at least one cassette one by one;
   a dyeing part including a pipette for insertion into the at least one cassette, for supplying a dyeing liquid to the at least one cassette and dyeing the slide glass with a sample smeared thereon and means for automatically smearing the sample and subsequently while the slide glass is in the at least one cassette, automatically dyeing the sample.

2. An automatic sample preparing apparatus according to claim 1 wherein:
   the at least one cassette comprises a hanging support part connected to the holding part for supporting the holding part in a hanging state.

3. An automatic sample preparing apparatus according to claim 1 wherein:
   the holding part of the at least one cassette comprises a main space for holding a slide glass and a liquid, an auxiliary space for liquid supply and discharge disposed adjacent to the main space and connected to the main space, and a bottom wall extending across the main space and the auxiliary space and sloping downward from the main space toward the auxiliary space.

4. An automatic sample preparing apparatus according to claim 1 wherein:
   the holding part of the at least one cassette comprises a positioning part for holding a slide glass in a position on one side of the inside of the holding part.

5. An automatic sample preparing apparatus according to claim 1 wherein:
   the at least one cassette is provided with a mis-setting prevention part for preventing the at least one cassette from being set other than in a predetermined state, said predetermined state including a predetermined orientation and predetermined position.

6. An automatic sample preparing apparatus according to claim 1 wherein:
   the loading part comprises a slide glass holding part for holding a smeared slide glass substantially horizontally, a stopping mechanism for temporarily stopping cassettes on the carrying part one by one, a pivoting mechanism for reversibly pivoting to a substantially horizontal position a cassette temporarily stopped by the stopping mechanism and a moving and inserting mechanism for moving a smeared slide glass held by the slide glass holding part and inserting it into the cassette pivoted to a substantially horizontal position by the pivoting mechanism.

7. An automatic sample preparing apparatus according to claim 1, further comprising:
   a storing part for storing cassettes holding smeared slide glasses fed out from the dyeing part.

8. An automatic sample preparing apparatus according to claim 1, wherein the at least one cassette includes a pipette opening, so that the pipette can be inserted into the at least one cassette.

9. An automatic sample preparing apparatus according to claim 1, wherein the carrying part includes two separate belts.

10. An automatic sample preparing apparatus according to claim 9, wherein said belts are positioned at substantially right angles to each other.

11. An automatic sample preparing apparatus according to claim 9, wherein the at least one cassette includes means for holding, the at least one cassette vertically to the two belts.

* * * * *